(12) United States Patent
Frey et al.

(10) Patent No.: US 6,753,424 B1
(45) Date of Patent: Jun. 22, 2004

(54) CONJUGATES OF DNA INTERACTING GROUPS WITH STEROID HORMONES FOR USE AS NUCLEIC ACID TRANSFECTION AGENTS

(75) Inventors: Felix Frey, University of Berne, Department of Internal Medicine, Freiburgstrasse, CH-3010 Bern (CH); Sandro Rusconi, University of Fribourg, Biochemistry, Pérolles, CH-1700 Fribourg (CH); Brigitte Frey, Bern (CH); Hans-Ueli Wehrli, Bern (CH)

(73) Assignees: Felix Frey, Berne (CH); Sandro Rusconi, Fribourg (CH)

( * ) Notice: Subject to any disclaimer, the term of this patent is extended or adjusted under 35 U.S.C. 154(b) by 0 days.

(21) Appl. No.: 09/762,871

(22) PCT Filed: Aug. 19, 1999

(86) PCT No.: PCT/CH99/00384

§ 371 (c)(1),
(2), (4) Date: Mar. 26, 2001

(87) PCT Pub. No.: WO00/11018

PCT Pub. Date: Mar. 2, 2000

(30) Foreign Application Priority Data

Aug. 21, 1998 (WO) ................................ PCT/IB98/01306

(51) Int. Cl.⁷ ............................................... C07J 17/00
(52) U.S. Cl. .................................................... 540/115
(58) Field of Search .......................... 552/574; 540/115

(56) References Cited

U.S. PATENT DOCUMENTS

| | | | |
|---|---|---|---|
| 5,547,932 A | 8/1996 | Curiel et al. ................... | 435/65 |
| 5,614,503 A | 3/1997 | Chaudhary et al. ............ | 514/44 |

FOREIGN PATENT DOCUMENTS

| | | |
|---|---|---|
| WO | WO 94/23751 | 10/1994 |
| WO | WO 96/03875 | 2/1996 |
| WO | WO 96/18372 | 6/1996 |

OTHER PUBLICATIONS

Ponpipom et al., "Cell–Specific Ligands for Selective Drug Delivery to Tissues and Organs." J. Med. Chem., vol. 24, pp. 1388–1395, 1981.*

Acedo et al., "Preparation of Oligonucleotide–Dexamethasone conjugates," *Bioorganic & Medicinal Chemistry Letters,* 5(15):1577–1580 (1995).

Chidambaram et al., "Targeting of antisense: synthesis of steroid–linked and steroid–bridged oligodeoxyribonucleotides," *Chemical Abstracts,* XP–002092511, 125(5):1208 (1996).

Haensler et al., "Synthesis and Characterization of a Trigalactosylated Bisacridine Compound to Target DNA to Hepatocytes," *Bioconjugate Chem.,* 4:85–93 (1993).

Wagner et al., "DNA–Binding Transferrin Conjugates as Functional Gene–Delivery Agents: Synthesis by Linkage of Polylysine or Ethidium Homodimer to the Transferrin Carbohydrate Moiety," *Bioconjugate Chem.,* 2(4):226–231 (1991).

\* cited by examiner

*Primary Examiner*—Barbara P. Badio
(74) *Attorney, Agent, or Firm*—Marshall, Gerstein & Borun LLP

(57) ABSTRACT

The present invention relates to novel compounds comprising a steroid hormone linked to a DNA-interacting molecule that target nucleic acids to the cell nucleus. Further, the invention relates to a method for introducing nucleic acids into the nucleus of cells with the help of such compounds. Pharmaceutical preparations containing such compounds and the use of such compounds for gene therapy are also provided.

8 Claims, No Drawings

CONJUGATES OF DNA INTERACTING GROUPS WITH STEROID HORMONES FOR USE AS NUCLEIC ACID TRANSFECTION AGENTS

FIELD OF THE INVENTION

The present invention provides novel compounds that target nucleic acids to the cell nucleus. Further, this invention generally relates to the transformation of cells, particularly mammalian cells, with exogenous DNA or other nucleic acids. More particular, the invention relates to a method for introducing nucleic acids into the nucleus of cells with the help of such compounds. In addition pharmaceutical preparations containing such compounds and the use of such compounds for gene therapy are also in the field to which the invention relates.

BACKGROUND OF THE INVENTION

All references cited herein in short form are outlined in detail in the list of references. The use of gene therapy to treat diseases of both genetic and infectious origin has increasingly become the focus of biomedical research. Accordingly, there have been numerous attempts to develop appropriate delivery systems, based on either recombinant viruses or non-viral vectors.

Several methods have been developed for introducing exogenous DNA molecules into eukaryotic cells for the production of transiently-and stably transfected cells. These methods include physical and chemical systems such as electroporation, microinjection, dextran, liposomes, calcium phosphate or polyethylenimine (PEI) mediated DNA uptake or cell fusion, and microprojectile bombardment. In addition, viral vectors have been used for DNA delivery into cells.

Although physical and chemical methods relatively efficiently overcome the plasma membrane of the cell, it is still unclear how DNA introduced into the cell by these methods penetrate the nuclear envelope. One of the current hypothesis is that the exogenous DNA that survives cytoplasmic degradation is incorporated into the nascent nucleus during cell division. Thus, cytoplasmic degradation as well as the capability of a transfected cell to divide will limit the efficacy of DNA uptake into the nucleus. Furthermore, quiescent, non-dividing cells are rarely transformed by these methods. However, targeting of quiescent cells is of primary importance for somatic gene therapy since a large proportion of somatic cells are non-dividing.

Another limitation of conventional physical and chemical methods is that they cannot provide specificity for particular cell types, i.e. by using a receptor mediated uptake approach. However, this is a highly desired goal if particular cells are to be targeted in tissues or intact organisms, as e.g. in gene therapy applications.

In an attempt to overcome some of the above drawbacks recombinant viral vectors are used for cell transformation. For example, viral systems derived from Adenovirus, Adeno-associated virus, Herpes simplex virus and HIV are being evaluated for targeting of quiescent cells. However, such viral systems pose various problems that are well-known in the art regarding safety in production and application, production costs, efficiency of transfection, duration of expression and amount of DNA that can be packaged, depending on the particular approach used. For example, the use of adenoviral systems is limited by the induction of immune responses to viral antigens with subsequent clearance of transducted cells, thereby strongly diminishing the prospects for long term gene expression. A major safety issue when viral vectors are used is i.e. the generation of replication competent particles during the in vivo packaging of recombinant viruses. This problem is absent if non-viral gene transfer systems are used.

A major advantage of some viral gene delivery systems as compared to conventional physical and chemical methods is the ability of viral vectors to target their DNA-load to the nucleus of the transduced cell, thereby increasing transformation efficiency.

An approach to target DNA into the cell nucleus would be to make use of the cell's own transport mechanisms that specifically guide cytoplasmic molecules through the nuclear pore into the nucleus. In example, certain transcription factors upon activation specifically translocate into the nucleus and, thus, such transcription factors could be used to target molecules to the nucleus. Steroid hormone receptors are an example of transcription factors located in the cytoplasm. They are activated by the binding of steroid hormones and subsequently localize to the nucleus. Use of these receptors for gene delivery systems could therefore accomplish nuclear targeting of the transfected DNA. Via nuclear targeting of the transfected DNA cells could be transfected more efficiently, because breakdown of the nuclear envelope during cell division would not be required to incorporate the transfected DNA. In particular, non-dividing cells could be transformed more efficiently. In addition, cellular targeting the DNA exclusively to cells that express the particular receptor used could be accomplished.

Petros et al. (WO 96/03875) describe a gene delivery system for nucleic acids to cells that comprises a steroid moiety capable of binding to an androgen receptor, wherein the steroid moiety is covalently linked lo a cationic salt, i.e. poly-L-lysine via an ester, an amide or a disulfide bond.

Efficient transformation of cells with this approach is largely dependent on the intracellular stability of the complexes administered. Intracellular conditions, such as i.e. pH, ionic concentrations and the presence of degrading enzymes are some of the limiting factors of intracellular stability of a compound. For example, if ester bonds are present in the complex they could be attacked by intracellular esterases. Further, unfavorable pH and ionic conditions may destabilize ionic linkages, e.g. when polycationic compounds such as poly-L-lysine are used to complex the DNA.

Another factor that may determine the success of a steroid mediated gene delivery approach is the maintenance of a high binding affinity between the steroid moiety and the steroid receptor after the derivatization of the steroid. The size of the DNA interacting moiety, the position of the linkage between the steroid and the DNA interacting moiety, as well as the steric properties of the linking bond itself, may, among others, determine whether steric hindrance of the steroid/steroid receptor interaction will occur after derivatization of the steroid. Further, complexing of the DNA to the DNA interacting moiety should be achieved at specific positions of the DNA molecule in order to avoid inactivation of the genes to be transcribed. For example, complexing the DNA by intercalation may randomly inactivate portions of the DNA. Further, the intercalating positions may even change after initial linkage was achieved, thereby preventing the use of two-step approaches that in a first step will link the DNA interacting moiety to a particular, i.e. non-transcribed DNA region and in a second step will ligate or clamp via bifunctional triple helix formers the functional genes to the complexed DNA region to avoid their inactivation. Also, complexation via cationic moieties interacting with the negatively charged DNA are random and may involve functionally important stretches of the DNA and thus interfere with the transcription of the complexed DNA.

A steroid mediated gene delivery system that combines high intracellular stability and a high binding affinity for the steroid receptor as well as the possibility for specific linkage to the desired DNA molecule has not been reported to date. Thus, there exists a continuous need for such a delivery system which is useful for the introduction of nucleic acids into the nuclei of cells, e.g., for the expression of therapeutical genes. The object of the present invention is therefore to provide such a novel system and new methods for introducing nucleic acids into the nuclei of cells, in particular mammalian cells.

SUMMARY OF THE INVENTION

The present invention provides for a compound comprising a steroid hormone linked to a DNA-interacting molecule. In a preferred embodiment, the steroid hormone is stably linked to the DNA-interacting molecule. This compound is useful for complexing with nucleic acids desired to be delivered to target cells.

In a further embodiment, the compound comprises a spacer between the steroid hormone and the DNA-interacting molecule.

This invention includes compounds, wherein the steroid hormone is selected from the group consisting of one or more of androgens, gestagens, oestrogens, glucocorticoids, mineralocorticoids, retinoids, thyroids or synthetic steroids.

Further included are compounds, wherein the DNA-interacting molecule is selected from the group consisting of one or more of intercalating agents, crosslinking reagents, incorporating molecules and ionically interacting molecules. In a preferred embodiment the DNA-interacting molecule is a psoralen.

In a further aspect the invention relates to a method for the preparation of the compound comprising the steps of ligating a steroid hormone to a DNA-interacting molecule. Such a method may involve the steps of ligating a spacer to the steroid hormone and ligating the DNA-interacting molecule to the spacer.

Furthermore, the present invention provides compounds that are complexed to a DNA molecule. In another aspect, this invention provides a method for the preparation of the complex comprising the steps of ligating a steroid hormone to a DNA-interacting molecule to form a compound and complexing the compound with a DNA molecule. This method may further comprise the steps of ligating a spacer to the steroid hormone and ligating the DNA-interacting molecule to the spacer.

In yet another aspect, the invention relates to the use of the compound for introducing a DNA molecule into the nucleus of a cell, in particular, into the nucleus of a non-dividing cell. A cell transfected with a complex of the invention as well as the use of such a cell for the medical treatment of a human being is also provided.

The invention also provides a pharmaceutical preparation comprising the complex of the invention and a physiologically tolerable carrier.

The invention further provides a method for transfecting cells comprising the step of administering a therapeutically effective amount of a complex of the invention to a subject.

It is still another object of the invention to provide an assay comprising the steps of a) transfecting cells with a complex of the invention, wherein the DNA molecule contains an expressible gene; b) monitoring the expression of said expressible gene, and c) comparing the expression of said expressible gene in transfected cells with the expression of said expressible gene in non-transfected cells.

DETAILED DESCRIPTION OF THE INVENTION

The term "steroid hormone" as used for the purposes of the present invention includes other hormones or lipophilic ligands with unrelated structures and physiological purposes that function at the molecular level in a similar way to the steroid hormones. Thus, each molecule that is a small molecule that binds to a specific intracellular receptor that upon activation translocates to the nucleus of the cell is comprised in the meaning of a "steroid hormone" of the invention. Examples of such molecules other than androgens, gestagens, oestrogens, glucocorticoids, mineralocorticoids or synthetic steroids, in particular dexamethasone, are retinoids such as retinoic acid and 9-cis retinoic acid, thyroid hormones and vitamin D and their derivatives.

A steroid hormone of the invention is derivatized by stably linking it to a molecule that has the capability to interact with nucleic acids (referred to as "DNA-interacting molecule"). The derivatized steroid then may be complexed with a nucleic acid via its DNA-interacting moiety ("nucleic acid/compound complex", herein also referred to as the "complex" of the invention). The DNA molecule may be complexed to one or more compounds via intercalation, crosslinking, incorporation, ionical or hydrophobical interaction. Thus "to complex" according to this invention includes linking the nucleic acid by ionical, hydrophobic and covalent interaction, and, accordingly, a complex of the invention includes all molecules wherein a compound of the invention is linked to a nucleic acid, independent of the chemical type of linkage/bond formation.

The nucleic acid/steroid complex of the invention can be transfected into cells and bind to the cytosolic steroid hormone receptors, which subsequently mediate nuclear localization of the complex. The nuclear localization of transfected DNA will enable the expression of genes encoded by the nucleic acids. The present invention thereby provides an improved method for delivering nucleic acids to the nuclei of cells, in particular, mammalian cells, e.g. exogenous DNA for transforming human cells. This improved method for example generally comprises providing to the cell targeted for transformation a specifically designed nucleic acid/compound complex, comprising the exogenous DNA desired to be targeted to the nucleus and expressed in the transformant.

The present invention provides compounds to form complexes with nucleic acids and the nucleic acid/compound complexes themselves. The present invention further provides an improved method for transforming cells with exogenous nucleic acids such as e.g. DNA, using such nucleic acid/compound complexes. This method combines positive attributes of viral (cell type specificity, nuclear targeting) and non-viral (convenience of preparation and application, safety, less limitations as to DNA size) methods of transfection and subsequent transformation.

According to the invention, the nucleic acid/compound complex comprising the exogenous nucleic acid, such as e.g. an steroid hormone linked to a DNA sequence encoding a therapeutic gene, may be delivered to the cell by means such as, but not restricted to, electroporation, microinjection, induced uptake, microprojectile bombardment, liposomes, viral vectors or other means as are known in the art. Accordingly, the present invention provides novel means for the in vivo and ex vivo/in vitro transformation and integration of exogenous nucleic acids desired to be expressed within hosts or host cells, particularly for the purpose of gene therapy. In one embodiment the 11β-hydroxysteroid dehydrogenase (11β-OHSD) gene is transfected into and expressed in 11β-OHSD deficient cells for the treatment of Apparent Mineralocorticoid Excess (AME). AME is characterized by an impaired conversion of cortisol by the enzyme 11β-hydroxysteroid deghydrogenase and is associated with a severe low renin, low aldosterone and hypertension with hypokalemia.

In the course of the experiments which led to the present invention it has been found that cells can efficiently be transformed by using a nucleic acid/compound complex of the invention.

The DNA-interacting molecule of the compound may be selected from the group consisting of one or more of intercalating agents, crosslinking reagents, incorporating molecules, tonically or hydrophobically interacting molecules. Preferred is a compound wherein the DNA-interacting molecule is psoralen (aminotrioxsalen). Psoralen is a molecule that can be specifically crosslinked to parts of a DNA molecule after photoactivation. Preferred ionically interacting molecules of the invention are polycations, in particular spermidine, spermine, polylysine and protamine.

A steroid hormone according to the invention may be "linked" to a DNA-interacting molecule directly via a covalent, ionic or hydrophobic interaction. In the alternative, it may be indirectly linked to a DNA-interacting molecule with a "spacer" being positioned between the steroid hormone and the DNA-interacting molecule. Compounds including a spacer between the steroid hormone and the DNA-interacting molecule are preferred. A "spacer" of the invention may for example be selected from the group of dicarbonic acids, i.e. succinates, in particular a hemisuccinate, ether, and thioether, amino acids, amines etc. In a preferred embodiment urethanes are spacers used in this invention. The compound may preferably comprise a spacer between the steroid hormone and the DNA-interacting molecule comprising more than two atoms. More preferred is a spacer comprising 2–30 atoms, particularly preferred is a spacer having 5–15 atoms. Most preferred is a spacer having 9 to 11, and in particular 10 atoms. Preferred are spacers wherein the atoms are C, O, N and S; spacers containing —S—S— or —O—O— are excluded from this invention. Within the meaning of the present invention, the spacer comprises the atoms between the first carbon atom which is not derived from the steroid hormone, as well as the first carbon atom derived from the DNA-interacting molecule, and it further includes said first atoms not derived from either the steroid hormone or the DNA-interacting molecule. For example, within the meaning of this invention, the spacer of Formula 29 which links Dexamethasone and Spermidine has a length of 10 atoms.

In a preferred embodiment of this invention the link is stable within the intracellular environment to which it exposed after cellular uptake. In another preferred embodiment of this invention the link is stable within blood serum or plasma. In particular, the link is stable under acidic (pH 5) and alkaline (pH 9) conditions, by proteinase K (pH 7.8, 50 μg/ml) and dispase (2.4 U/ml) digestion and after incubation with cellular extracts and with DMEM/10% FCS.

The bond linking the steroid to the spacer or the DNA-interacting molecule may be positioned depending on their chemical accessibility and on their influence on the affinity for the cognate receptor. Preferred are positions either at carbon atom 1, 2, 4, 6, 7, 11α, 12, 15, 16, 17 or 21 if the steroid hormone is a glucocorticoid. If the steroid hormone is an androgen, positions 1, 2, 4, 6, 7, 11α, 12, 15, 16, 17 are preferred. Preferred is an urethane bond positioned either at carbon atom 6 or 21 of a glucocorticoid. More preferred is an urethane bond positioned at carbon atom 21 of a glucocorticoid.

The present invention thus provides for a compound comprising a steroid hormone linked to a DNA-interacting molecule. In a preferred embodiment, it is stably linked to the DNA-interacting molecule via a covalent bond, e.g. a urethane bond, a thiourethane bond, a sulfonate, or an ether bond. These covalent bonds provide for high intracellular stability of the compound as well as serum/plasma stability. In a preferred embodiment the bond is a urethane bond. In a more preferred embodiment the steroid hormone is linked via a first urethane bond to a spacer and the spacer is linked via a second urethane bond to the DNA-interacting molecule.

The present invention further provides a method for the preparation of a complex comprising the steps of ligating a steroid hormone to a DNA-interacting molecule to form a compound and complexing the compound with a DNA molecule. The method may further comprise the steps of ligating a spacer to the steroid hormone and ligating the DNA-interacting molecule to the spacer. Most preferred is the method wherein the steroid hormone is linked via an urethane bond to the DNA-interacting molecule. Depending on the DNA-interacting molecule used, the DNA molecule may be complexed to one or more compounds via intercalation, crosslinking, incorporation, ionical or hydrophobical interaction. In a preferred embodiment the DNA molecule is crosslinked to the compounds. In a preferred embodiment the crosslinking reagent is psoralen. To achieve "incorporation" the steroid is conjugated via a suitable spacer to a desoxy-ribonucleotide triphosphate which is then build into a DNA molecule by a polymerase-mediated protocol, i.e. nick-translation, 5' overhangs filling or PCR incorporation.

In one embodiment this invention relates to the use of the compound for introducing a DNA molecule into the nucleus of a cell, in particular a non-dividing cell, and in a particular embodiment, a quiesent somatic cell.

A method for transfecting cells comprising the step of administering a therapeutically effective amount of a nucleic acid/compound complex to a subject, in particular a human being, is also provided by the present invention. In an embodiment the 11β-hydroxysteroid deghydrogenase (11β-OHSD) gene is administered in a therapeutically effective amount in 11β-OHSD deficient cells for the treatment of Apparent Mineralocorticoid Excess (AME). This invention includes, but is not limited to the delivery of, for example, mammal-specific genes, such as the insulin gene, the somatostatin gene, the interleukin genes, the t-PA gene, etc. Apart from naturally occurring structural genes that code for a useful and desirable property or a pharmacological agent, within the scope of this invention it is also possible to use genes that have been modified previously in a specific manner using chemical or genetic engineering methods.

The term "DNA" or "nucleic acid" as a component of the "nucleic acid/steroid complex" according to the present invention may be any type of nucleic acid, for example RNA, modified RNA or DNA, wherein DNA is the preferred form. For example, the present invention particularly provides an improved method for transiently transfecting and for stably transforming cells with exogenous nucleic acids such as e.g. the 11β-hydroxysteroid deghydrogenase gene. The term "exogenous" DNA or nucleic acid used herein is meant to include any DNA or other nucleic acid that has been obtained by recombinant nucleic acid technology. The exogenous DNA to be used in the process according to the invention for transforming cells may be either of homologous or heterologous origin with respect to the cell type involved or it may be of synthetic origin or both. The coding DNA sequence can be constructed according to conventional methods, e.g. from genomic DNA, or from cDNA. Another possibility is the construction of a hybrid DNA sequence consisting of both cDNA and genomic DNA and/or synthetic DNA. The cDNA may originate from the same gene as the genomic DNA, or alternatively both the cDNA and the genomic DNA may riginate from different genes. In any case, however, both the genomic DNA and/or the cDNA may each be prepared individually from the same or from different genes. The term DNA or nucleic acid includes (a) DNA sequences that have been been prepared entirely or at least partially by chemical means and (b) antisense or sense oligonucleotides. For example, synthetic DNA sequences may be suitably used, e.g. for modifying native DNA sequences in terms of codon usage, expression efficiency, etc. If the DNA sequence to be transformed into the recipient animal cell contains portions of more than one gene, these genes may originate from one and the same organism, from several organisms that belong to more than one strain, one variety or one species of the same genus, or from organisms that belong to more than one genus of the same or of another taxonomic unit.

In a particular embodiment of this invention the DNA complexed to the compound of the invention may be used as a link to another DNA that contains i.e. a therapeutic gene. For example, the DNA that contains i.e. a therapeutic gene-may be directly ligated or clamped i.e. via bifunctional triple helix formers to the stretch of DNA that has been complexed to the compound of the invention.

Chimeric recombinant DNA molecules that comprise an expressible DNA, but especially a structural gene, preferably a heterologous structural gene operably linked with expression signals active in animal cells, such as enhancer, promoter and transcription termination sequences, as well as, optionally, with further coding and/or noncoding sequences of the 5' and/or 3' region such as e.g. signal sequence may also be preferably used within the transformation process as part of the nucleic acid/compound complex used according to the present invention. It is often advantageous to incorporate a leader sequence between the promoter sequence and the adjacent coding DNA sequence, the length of the leader sequence being so selected that the distance between the promoter and the DNA sequence to be expressed is the optimum distance for expression of the associated structural gene.

The expression signals active in mammalian cells usually comprise a promoter that is recognised by the host organism and is operably linked to the DNA to be expressed in the transformant. Such a promoter may be inducible or constitutive. The promoters are operably linked to said DNA by removing the promoter from the source DNA by restriction enzyme digestion and combining the isolated promoter sequence with the expressible DNA sequence. Both the native promoter sequence of the structural gene of interest and many heterologous promoters may be used to direct amplification and/or expressionl of said structural gene. Suitable promoters for animal and in particular mammalian hosts are those derived from the genomes of viruses such as polyoma virus, adenovirus, fowlpox virus, bovine papilloma virus, avian sarcoma virus, Rouse sarcoma virus (RSV), cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with structural gene sequence to be expressed, provided such promoters are compatible with the host cell systems.

The transcription of an exogenous DNA encoding the desired structural gene can be increased by inserting an enhancer sequence into the DNA as a component of the nucleic acid/compound complex according to the invention. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the recombinant chimeric sequence at a position 5' or 3' to the coding DNA sequence, but is preferably located at a site 5' from the promoter.

Host cells to which nucleic acids can be delivered by a method according to the invention include insect and vertebrate cells. In recent years propagation of vertebrate ceils in culture (tissue culture) has become a routine procedure. Examples of useful vertebrate host cell lines are epithelial or fibroblastic cell lines such as Chinese hamster ovary (CHO) cells, COS1 cells (monkey kidney cells transformed with SV40 T-antigen), CV1 cells (parent line of the former), Rat1 (rat fibroblast) cells, NIH 3T3 cells, HeLa cells, LLC-Pk1 (pig kidney epithelial) cells or 293T cells. The host cells referred to in this disclosure comprise cells in in vitro/ex vivo culture as well as cells that are within a host animal.

Especially suitable for use in the process according to the invention are all those structural genes which upon expression produce proteins or polypeptides which are beneficial for the transformed cells, tissues or mammals, e.g. which compensate eventual mutatations, or which have pharmacological properties and could be used as pharmaceutical agents in the treatment of diseases. Examples for such structural genes include those encoding hormones, immunomodulators and other physiologically active substances.

Furthermore, the broad concept of the present invention also includes genes that are produced entirely or partially by chemical synthesis. Genes or DNA sequences that may be used within the scope of the present invention are therefore both homologous and heterologous gene(s) or DNA and also synthetic gene(s) or DNA according to the definition given within the scope of the present invention.

Alternatively, oligonucleotides can be used corresponding in sequence to a cellular sequence to be targeted, either in the same coding direction, as such or carrying a mutation, or in the antisense coding direction.

Possible methods for the direct transfer of the nucleic acid/compound complex according to the invention into a cell comprise, for example, the treatment of cells using procedures that modify the plasma membrane, for example, polyethylene glycol treatment, liposome-based technologies, heat shock treatment or electroporation, or a combination of those procedures (see e.g. Chu et al. (1987); Hodgson and Solaiman (1996), Shillito et al. (1985)).

In the electroporation technique animal cells together with the nucleic acid/compound complex used according to the invention are subjected to electrical pulses of high field strength. This results in a reversible increase in the permeability of biomembranes and thus allows the insertion of the nucleic acid/compound complex according to the invention. Electroporated cells renew their cell membrane, divide and form aggregates or monolayers of transformed cells. Selection of the transformed cells can take place with the aid of the above-described phenotypic markers.

Also suitable for the transformation of mammalian cells is direct gene transfer using co-transformation (Schocher R J et al, (1986)). Co-transformation is a method that is based on the simultaneous taking up and integration of various DNA molecules (non-selectable and selectable genes) into the genome and that therefore allows the detection of cells that have been transformed with non-selectable genes.

Further, means for inserting the nucleic acid/compound complex used according to the invention directly into a cell comprise using purely physical procedures, for example by microinjection using finely drawn micropipettes or by bombarding the cells with microprojectiles that are coated with the transforming or transiently transfecting nucleic acid (Wang Y-C et al, (1988)) or are accelerated through a nucleic acid containing solution in the direction of the cells to be transformed by a pressure impact thereby being finely atomized into a fog with the solution as a result of the pressure impact (EP-A434,616). Microprojectile bombardment has been advanced as an effective transformation technique for animal cells.

The list of possible transformation and transfection methods given above by way of example is not claimed to be complete and is not intended to limit the subject of the invention in any way.

The method according to the invention can be advantageously used to increase the transformation efficiency of transformation processes, in that, for example, less transforming DNA is needed as compared to the conventional techniques. Additionally, the present invention can be used for somatic gene therapy in humans, which use is also part of the invention.

In various alternative embodiments of the present invention, therapeutic compositions useful for practicing the therapeutic methods described herein are contemplated. As used herein, the terms "therapeutic compositions" and "pharmaceutical preparations" are used interchangeably. Therapeutic compositions of the present invention may contain a physiologically tolerable carrier together with one or more therapeutic nucleic acid/compound complexes of this invention, dissolved or dispersed therein as an active ingredient. The nucleic acid/compound complexes in the therapeutic compositions may have been combined with/ introduced into a transfecting agent. A "transfecting agent" in the sense of this invention may be any agent presently known or unknown that improves transfection of mammalian cells when administered as part of or together with a DNA to be transfected. Thus, the present invention comprises therapeutic compositions useful in the specific targeting of as well as in delivering a therapeutic nucleotide sequence to those cells. In a preferred embodiment, the therapeutic composition is not immunogenic or otherwise able to cause undesirable side effects when administered to a subject for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a subject, e.g., a mammal, without the production of undesirable physiological effects such as nausea, dizziness, gastric upset and the like.

The preparation of a pharmacological composition that contains active ingredients dissolved or dispersed therein is well understood in the art. Typically such compositions are prepared as injectables, either as liquid solutions or suspensions. However, solid forms suitable for solution or suspension in liquid prior to use can also be prepared. A preparation can also be emulsified, or formulated into suppositories, ointments, creams, dermal patches, or the like, depending on the desired route of administration.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof, including vegetable oils, propylene glycol, polyethylene glycol and benzyl alcohol (for injection or liquid preparations); and petrolatum (e.g., VASELINE), vegetable oil, animal fat and polyethylene glycol (for externally applicable preparations). In addition, if desired, the composition can contain wetting or emulsifying agents, isotonic agents, dissolution promoting agents, stabilizers, colorants, antiseptic agents, soothing agents and the like additives (as usual auxiliary additives to pharmaceutical preparations), pH buffering agents and the like which enhance the effectiveness of the active ingredient.

The therapeutic compositions of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions.

A therapeutic composition typically contains an amount of a nucleic acid/steroid complex of the present invention sufficient to deliver a therapeutically effective amount to the target tissue, typically an amount of at least 0.01 weight percent to about 1 weight percent of therapeutic nucleolide sequence per weight of total therapeutic composition. A weight percent is a ratio by weight of therapeutic nucleotide sequence to total composition. Thus, for example, 0.01 weight percent is 0.01 grams of DNA segment per 100 grams of total composition. However, lower concentrations i.e. 0,0001% can be used if DNA transfer reaches efficiencies comparable to viral transfer, higher concentrations i.e. up to 10% can be reached if special formulations allowing higher DNA solubility can be developed.

The nucleic acid/compound complexes of the present invention are particularly suited for gene therapy. Thus, various therapeutic methods are contemplated by the present invention. Methods of gene therapy are well known in the art (see, e.g., Larrick and Burck (1991); Kriegler (1990)). The term "subject" should be understood to include any animal, particularly mammalian, patient, such as any murine, rat, bovine, porcine, canine, feline, equine, ursine, or human patient.

When the foreign gene carried encodes a tumor suppressor gene or another anti-tumor protein, the compounds of the present invention are useful to treat or reduce hyperproliferative cells in a subject. Hyperproliferation and/or uncontrolled proliferation occurs first, in neoplastic diseases, second, in so-called immune mediated entities and third, in disease states with hyperplasia/hypertrophy. Examples of the first group are neoplasias such as breast cancer, bladder cancer, colon cancer, lung cancer, various leukemias, lymphomas, sarcomas and others. In particular, tumours that may produce steroid hormone receptors, such as colon cancer, rectal cancer, breast cancer, prostate cancer, endometrial cancer, ovarian cystadenocarcinoma, pancreatic cancer, lung cancer, in particular non-small cell lung cancer, gallbladder cancer and thyroid carcinoma are contemplated. To the second group belong among others rejection of transplanted organs, systemic immune mediated diseases such a lupus erythematodes, periartheritis nodosa, Wegeners disease, asthma, eczema etc. The third entity comprises etiologically often poorly understood local or diffuse organomegaly, such as benign prostatic hypertrophy, psoriasis, hypertrophic cardiomyopathy, thyroid hyperplasia etc.

In all these disease states the present approach will be of great interest whenever a particular ligand receptor is restrictively expressed in this target cell population.

Administration includes, but is not limited to, the introduction of therapeutic compounds (=compositions and complexes of the present invention) into a cell or subject via various means, including direct injection, intravenously, intraperitoneally, via intra-tumor injection, via aerosols, or topical administration, as disclosed herein may also be combined for administration of an effective amount of the compounds with a pharmaceutically-acceptable carrier, as described herein.

As used herein, "effective amount" of a therapeutic compound generally means the amount of therapeutic composition (or nucleic acid/steroid complexes or protein expression produced thereby) which achieves a positive outcome in the subject to whom the therapeutic compound is administered. The total volume administered will necessarily vary depending on the mode of administration, as those of skill in the relevant art will appreciate, and dosages may vary as well.

The present invention also contemplates methods of ameliorating pathologies characterized by genetic defects in a subject, by administering to the subject an effective amount of a therapeutic compound as described herein. The nucleic acid portion of such a therapeutic compound preferably contains a foreign gene encoding a gene product (e.g. polypeptide or protein) having the ability to ameliorate the pathology, under suitable conditions. As used herein, the term "genetic defect" means any disease, condition or abnormality which results from inherited and/or aquired changes causing directly disease states and/or predisposing to aquired and/or degenerative disease states. Groups of diseases comprise among others, disorders ot the carbohydrate metabolism, inborn errors of amino acid-, organic acid-, purine or pyrimidine-metabolism, lysosomal storage diseases, peroxysomal disorders, cystic fibrosis, sickle cell disease, AME or degenerative diseases presently poorly understood.

For in vitro gene transfer, administration is often accomplished by first isolating a selected cell population from a patient such as lung epithelial cells, lymphocytes and the like followed by in vitro gene transfer of the complex of this invention and the replacement of the cells into the patient. In vivo therapy is also contemplated, e.g., via the administration of therapeutic compositions of this invention by various delivery means. For example, aerosol administration and administration via subcutaneous, intravenous, intraperitoneal, intramuscular, ocular means and the like are also within the scope of the present invention. Other gene-delivery methods are also useful in conjunction with the methods, compositions and constructs of the present invention; see, e.g., published International Application No. WO 95/11984, the disclosures of which are incorporated by reference herein.

The present invention also contemplates various methods of targeting specific cells, e.g. cells in a subject in need of diagnosis and/or treatment. As discussed herein, the present invention contemplates that the compositions of the present invention may be directed to specific receptors or cells, in particular, steroid receptors and steroid receptor expressing cells, for the ultimate purpose of delivering DNA to the nuclei of specific cells or cell types. The compounds of the present invention are particularly useful in this regard. A special feature of the complexes used according to the invention is their ability to also target non dividing cells, due to their nuclear targeting potential.

The invention is further described, for the purposes of illustration only, in the following examples.

EXAMPLES

Example 1

In Vitro Displacement Assay to Measure the Binding Affinity of Compounds

A baculovirus encoding the rat glucocorticoid receptor (GR) is created. Then, a protocol to express about 50'000 molecules of GR per cell in this system is established. High levels of glucocorticosteroid binding in the cytosolic fraction of insect cells infected with the recombinant baculovirus are observed. By measuring the displacement of radiolabelled dexamethasone from the receptor through unlabelled glucocorticocompounds, it is possible to determine whether they can bind the GR as effectively or less effectively than cortisol or dexamethasone.

Example 2

In Vivo Reporter Assay to Test for Biological Activity of Compounds

The rat embryonal cell line 3Y1 (Kimura et al., 1975) contains reasonably high levels of glucocorticoid receptor (20'000 molecules-per cell). 3Y1 cells therefore represent a good model system to test glucocorticosteroid-mediated gene delivery. In addition, 3Y1 cells resemble normal cells in many ways, including karyotype of chromosomes, anchorage dependency and growth rate, and can be easily rendered quiescent by serum starvation. Furthermore, the Kiki cell line (a derivative of 3Y1) is engineered to carry a chromosomal copy of the bacterial β-galactosidase gene under control of the MMTV promoter, a known glucocorticoid dependent element. Upon exposure to active glucocorticoids, Kiki cells express β-galactosidase in a dose dependent manner (Satoh et al., 1993). Therefore, Kiki cells are used to test the biological activity of compounds.

Example 3
In Vivo Nuclear Translocation Induction Assay

Permanently transformed cell lines that express receptor/green fluorescent protein (GFP) are established. The receptor is i.e. the glucocorticoid receptor (GR) or mineralocorticoid receptor (MR). Upon exposure of the cell lines to compounds relative nuclear fluorescence is measured as compared to negative controls (no exposure to compounds). Cells exposed to cortisol or dexamehasone may serve as positive controls.

Example 4
In Vivo Reporter Assay to Test for Enhancement of Transfection/transformation A receptor containing cell line is exposed to a reporter DNA, i.e. a constitutive LacZ plasmid that is tethered to a compound. LacZ levels are measured and compared to controls, i.e. LacZ levels of cells contacted with compounds without tethered DNA are compared to LacZ levels of cells contact with free DNA (without linkage to a compound). Further, cells that do not have the steroid receptor may be used as negative controls.

Analogous assays to the examples 1–4 may be established for quiescent cells, i.e. with the use of primary fibroblasts instead of cell lines.

Example 5
Synthesis of Compounds

Abbreviations:
- HOAC=Acetic acid
- n-BuOH=n-Butanol
- DMF=N,N-Dimethylformamide
- AcOEt/EtOAc=Ethyl acetate
- MeOH=Methanol
- NMM=N-Methylmorpholine
- THF=Tetrahydrofuran
- p-TosH=p-Toluolsulfonic acid

Example 5.1
Preparation of:

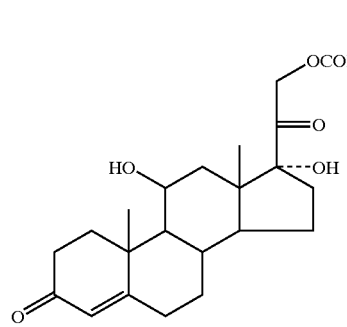

(=Formula 1)

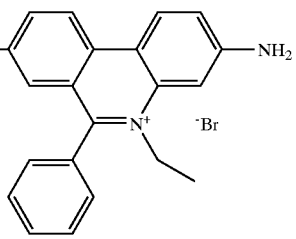

and the other regioisomere relating to the aminogroups of the ethidiumbromide.

20 mg 2-carboxy-ethyl-1-carboxamicacid-cortisol-21-ester dissolved in 1 ml THF are treated for 2 h at −20° C. with 9 µl isobutylchloroformate in presence of 15 µl NMM. After 2 h 17.4 mg ethidiumbromide are added and stirred for 24 h at 20° C. the mixture is then evaporated at 60° C. in a $N_2$-flow. The desired product is purified by TLC (n-BuOH:HOAc:$H_2O$=3:1:1 mixture; Rf=0.75); UV: 240 ($\epsilon$=15000), 298 ($\epsilon$=27800), 324 ($\epsilon$=12000).

Preparation of Starting Materials
Preparation of:

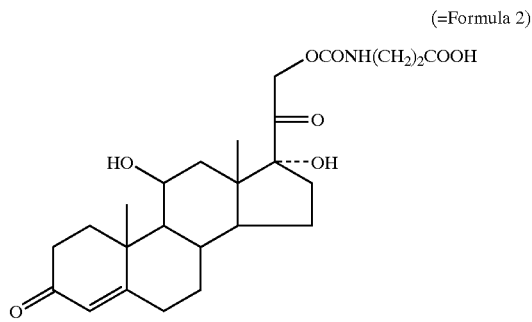

(=Formula 2)

200 mg 2-carboxymethyl-ethyl-1-carboxamicacid-cortisol-21-ester are stirred at 30° C. in a mixture of 9 ml methanol and 1 ml 10 n NaOH in $H_2O$. After 3 h the solution is acidified with 1 n HCl, extracted with EtOAc, washed with sat. aq. $NaHCO_3$ solution and dried over $Na_2SO_4$. After evaporation the crude product is used without purification.

Preparation of:

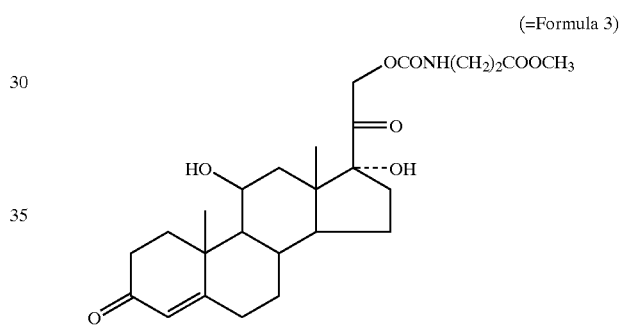

(=Formula 3)

73 mg cortisol and 44 µl NMM are stirred with 60 mg 4-nitrophenyl-chloroformate in 2.5 ml THF at 25° C. After 24 h a solution of 84 mg β-alanine-methyl-ester hydrochloride in 0.5 ml DMF and 76 µl NMM is added and stirred for additional 14 h. After that the mixture is diluted with AcOEt, washed with 1 n HCl, sat. aq. $NaHCO_3$-solution, sat. aq. NaCl-solution, dried over $Na_2SO_4$, and evaporated. The crude material is purified by silicagel-chromatography.

The product is eluated with toluene-AcOEt(4:1)-mixture.

TLC: AcOEt, Rf=0.61, UV: 240 nm ($\epsilon$=15500).

Example 5.2
Preparation of:

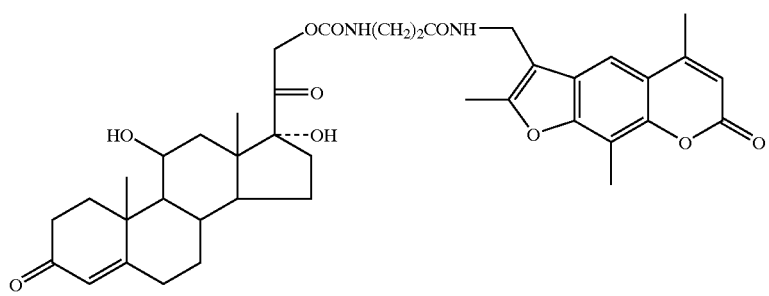
(=Formula 4)

10 mg 2-carboxy-ethyl-1-carboxamicacid-cortisol-21-ester (=Formula 2) dissolved in 1 ml THF are treated for 2 h at −20° C. with 4.5 µl isobutylchloroformate in presence of 7.5 µl NMM. After 2 h a solution of 5 mg 4'-aminomethyl-trioxalen hydrochloride in 1 ml DMF and 15 µl NMM is added and stirred for 24 h at 20° C. The mixture is then evaporated at 60° C. in a $N_2$-flow and the resulting residue chromatographed on silicagel. The desired product is eluated with AcOEt-MeOH(9:1)-mixture.

TLC: AcOEt-MeOH(9:1), Rf=0.15, UV: 247 (ε=33600), 295 (ε=9800), 335 (ε=6300).

Example 5.3
Preparation of:

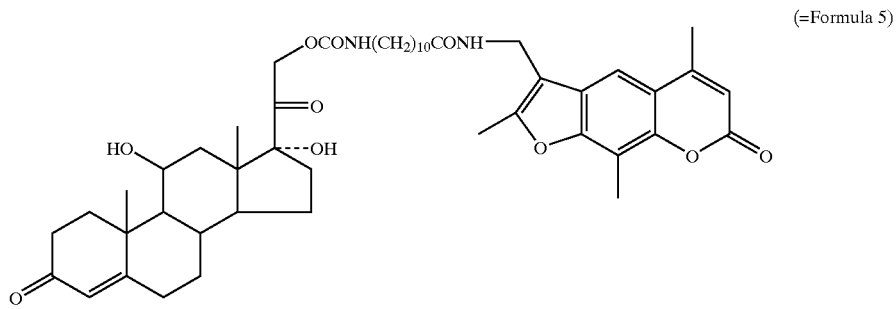
(=Formula 5)

10 mg 10-carboxy-n-decyl-1-carboxamicacid-cortisol-21-ester dissolved in 1 ml THF are treated for 2 h at −20° C. with 4.5 µl isobutylchloroformate in presence of 7.5 µl NMM. After 2 h a solution of 5 mg 4'-aminomethyltrioxalen hydrochloride in 1 ml DMF and 15 µl NMM is added and stirred for 24 h at 20° C. The mixture is then evaporated at 60° C. in a $N_2$-flow and the resulting residue chromatographed on silicagel. The desired product is eluated with AcOEt.

TLC: AcOEt, Rf=0.19, UV: 247 (ε=33300), 295 (ε=9700), 335 (ε=6100).

Preparation of Starting Materials
Preparation of:

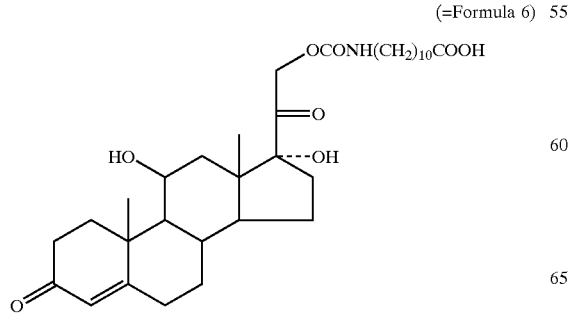
(=Formula 6)

300 mg 10-carboxymethyl-n-decy-1-carboxamicacid-cortisol-21-ester are stirred at 30° C. in a mixture of 13.5 ml MeOH and 1.5 ml 10 n NaOH in water. After 3 h the solution is acidified with 1 n HCl, extracted with EtOAc, washed with sat. aq. $NaHCO_3$ solution and dried over $Na_2SO_4$. After evaporation the crude product is used without purification.

Preparation of:

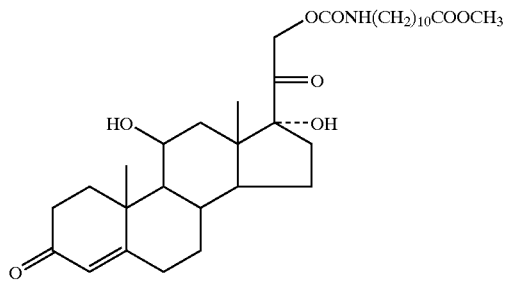
(=Formula 7)

146 mg cortisol and 88 µl NMM are stirred with 120 mg 4-nitrophenyl-chloroformate in 5 ml THF at room temperature. After 24 h a solution of 212 mg 11-amino-undecanoic-acid-methylester in 1 ml DMF and 152 µl NMM is added and stirred for additional 14 h. The mixture is then diluted with AcOEt, washed with 1 n HCl, sat. aq. $NaHCO_3$ solution, sat. aq. NaCl, dried over $Na_2SO_4$ and evaporated. The crude material is purified by silicagel chromatography. The product is eluated with toluene-AcOEt(4:1)-mixture.

TLC: AcOEt, Rf=0.79, UV: 240 (ε=15500).

Example 5.4

Preparation of:

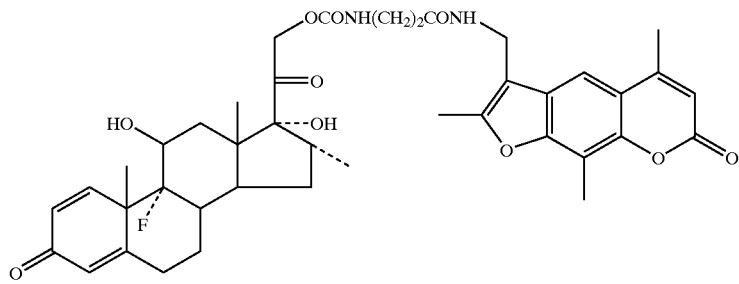

(=Formula 8)

5 mg 2-carboxy-ethyl-1-carboxamicacid-dexamethasone-21-ester dissolved in 1 ml THF are treated for 2 h at −20° C. with 4.3 µl isobutylchloroformate in presence of 3.73 µl N-MM. After 2 h a solution of 5 mg 4'-aminomethyltrioxalen hydrochloride in 1 ml DMF and 15 µl N-MM is added and stirred for 24 h at 20° C. The mixture is then evaporated at 60° C. in a $N_2$-flow and the resulting residue chromatographed on silicagel. The desired product is eluated with AcOEt.

TLC: AcOEt, Rf=0.25, UV: 249 ($\epsilon$=33500), 295 ($\epsilon$=9700), 335 ($\epsilon$=6250).

Preparation of Starting Materials

Preparation of:

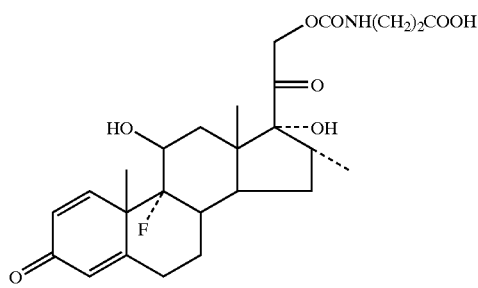

(=Formula 9)

390 mg 2-carboxymethyl-ethyl-1-carboxamicacid-dexamethasone-21-ester are stirred at 30° C. in a mixture of 20 ml methanol and 2 ml 10 n NaOH in water. After 2 h the solution is acidified with 1 n HCl, extracted with EtOAc, washed with sat. aq. $NaHCO_3$ solution and dried over $Na_2SO_4$. After evaporation the crude product is chromatographed on silicagel. The product is eluated with toluene-AcOEt(2:1).

UV: 240 ($\epsilon$=14900).

Preparation of:

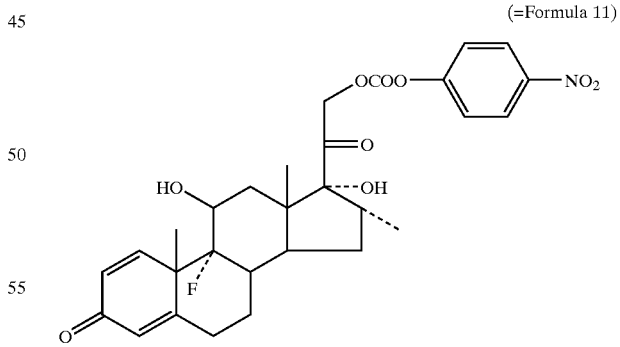

(=Formula 10)

500 mg dexamethasone-21-(4'-nitrophenyl-carbonate) are stirred with 192.2 mg β-alanin-methylester hydrochloride and 184.2 µl N-ethyidiisopropylamine in 2 ml MF for 6 h. The mixture is then diluted in AcOEt, washed with water dried over $Na_2SO_4$ and evaporated. The crude material is chromatographed on silicagel. The product is eluated with toluene-AcOEt(4:1).

TLC: AcOEt, Rf=0.73, UV: 242 ($\epsilon$=14400).

Preparation of:

(=Formula 11)

1.040 g dexamethasone are stirred in 40 ml THF at room temp. for 4 h with 1.240 g 4-nitrophenyl-chloro-formic-ester and 1.3 ml N-MM. The reaction mixture is diluted with AcOEt, washed with 1 n aq. HCl, sat. aq. $NaCO_3$-solution, sat. aq. NaCl-solution, dried over $Na_2SO_4$ and evaporated. The crude material is chromatographed on silicagel. The product is eluated with toluene-AcOEt(85:15).

TLC: toluene:AcOEt(1:1), Rf=0.9, UV: 242 ($\epsilon$=15300).

Example 5.5

Preparation of:

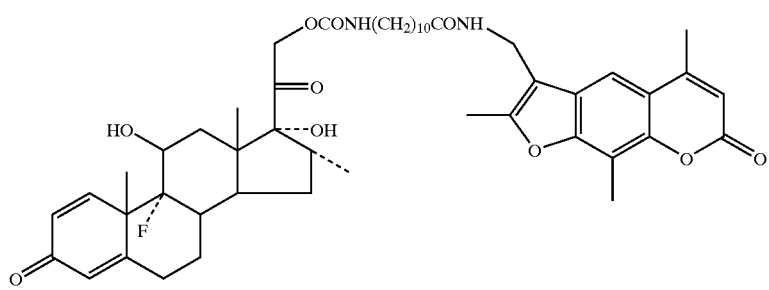

(=Formula 12)

6.3 mg 10-carboxy-n-decyl-1-carboxamicacid-dexamethasone-21-ester dissolved in 1 ml THF are treated for 2 h at −20° C. with 4.3 μl isobutylchloroformate in presence of 3.73 μl N-MM. After 2 h a solution of 5 mg 4'-aminomethyltrioxalen hydrochloride in 1 ml DMF and 15 μl N-MM is added and stirred for 24 h at 20° C. The mixture is then evaporated at 60° C. in a $N_2$-flow and the resulting residue chromatographed on silicagel. The desired product is eluated with Toluene-AcOEt(4:1).

TLC: AcOEt, Rf=0.88, UV: 247 (ε=32900), 295 (ε=9150), 335 (ε=6350).

Preparation of Starting Materials
Preparation of:

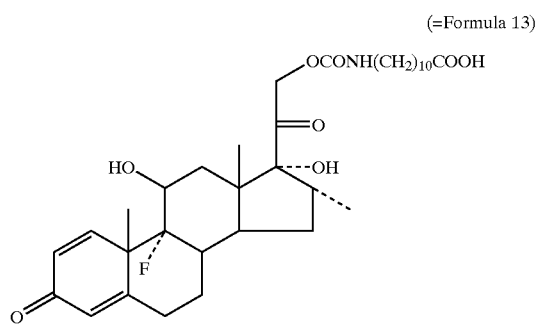

(=Formula 13)

360 mg 10-carboxymethyl-n-decyl-1-carboxamicacid-dexamethasone-21-ester are stirred at 30° C. in a mixture of 20 ml methanol and 2 ml 10 n NaOH in water. After 2 h the solution is acidified with 1 n HCl, extracted with EtOAc, washed with sat. aq. NaCl solution and dried over $Na_2SO_4$. Alter evaporation the crude product is chromatographed on silicagel. The product is eluated with toluene-AcOEt(2:1). UV: 241 (ε=15100).

Preparation of:

(=Formula 14)

[structure of Formula 14 with OCONH(CH₂)₁₀COOCH₃ group]

500 mg dexamethasone-21-(4'-nitrophenyl-carbonate) (=Formula 11) are stirred with 192.2 mg 11-amino-undecanoicacid-methylester and 184.2 μl N-ethyidiisopropylamine in 2 ml DMF for 6 h. The mixture is then diluted in AcOEt, washed with water, dried over $Na_2SO_4$ and evaporated. The crude material is chromatographed on silicagel. The product is eluated with toluene-AcOEt(4:1).

TLC: AcOEt, Rf=0.85, UV: 243 (ε=14700).

Example 5.6

Preparation of:

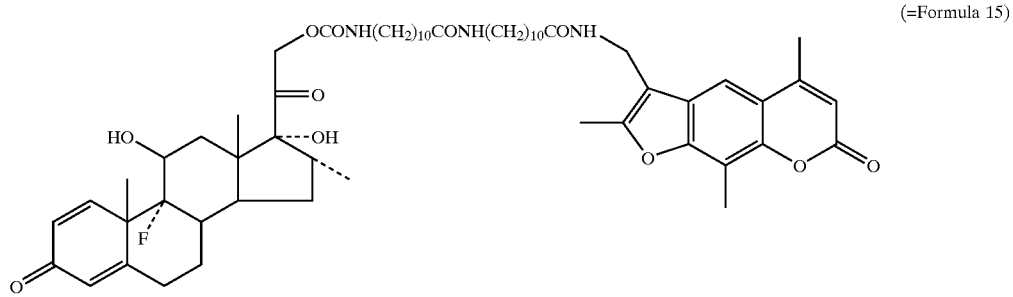

(=Formula 15)

7.9 mg compound of formula 16 dissolved in 1 ml THF are treated for 2 h at −20° C. with 2.22 μl isobutylchloroformate in presence of 2.8 μl NMM. After 2 h a solution of 5 mg 4'-aminomethyltrioxalen hydrochloride in 2 ml DMF and 15 μl NMM is added and stirred for 24 h at 20° C. The mixture is then evaporated at 60° C. in a $N_2$-flow and the resulting residue chromatographed on silicagel. The product is eluated with EtOAc.

TLC: AcOEt, Rf=0.29, UV: 248 )ε=32900), 295 (ε=9500), 335 (ε=6100).

Preparation of Starting Materials

Preparation of:

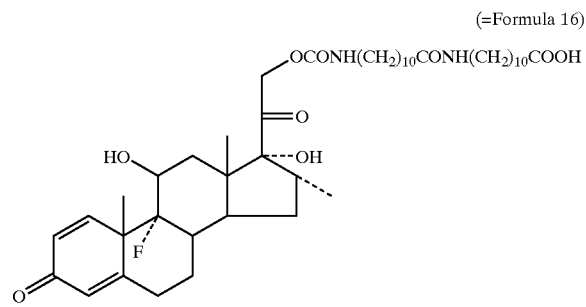
(=Formula 16)

150 mg compound of formula 17 are stirred at 30° C. in a mixture of 2 ml methanol and 0.4 ml 5 n aq. NaOH-solution. After 2 h the solution is acidified with 1 n HCl, extracted with EtOAc, washed with sat. aq. NaCl-solution and dried over $Na_2SO_4$. After evaporation the crude product is chromatographed on silicagel. The product is eluated with toluene-AcOEt(2:1)-mixture.

UV: 242 ($\epsilon$=13800).

Preparation of:

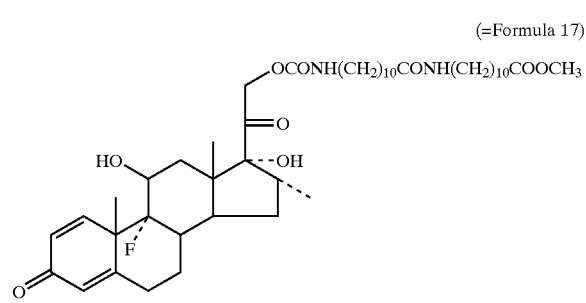
(=Formula 17)

160 mg dexamethasone-21-(4'-nitrophenyl-carbonate) (=Formula 11) are stirred with 170 mg compound of formula 18 and 180 µl N-ethyldiisopropylamine in 1 ml DMF for 6 h. The mixture is then diluted with AcOEt, washed with water, dried over $Na_2SO_4$, evaporated and chromatographed on silicagel. The product is eluated with toluene-AcOEt (1:1)-mixture.

TLC: AcOEt, Rf=0.68, UV: 240 ($\epsilon$=17300).

Preparation of:

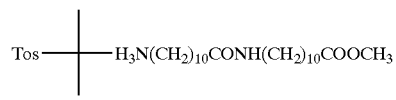
(=Formula 18)

Compound of formula 18 is prepared by a active-ester (isobutylchloroformate) condensation of BOC-aminoundecanoicacid with 11-aminoundecanoicacid-methylester followed by a cleavage of the BOC-group with p-toluenesulfonicacid in acetonitrile.

Example 5.7

Preparation of:

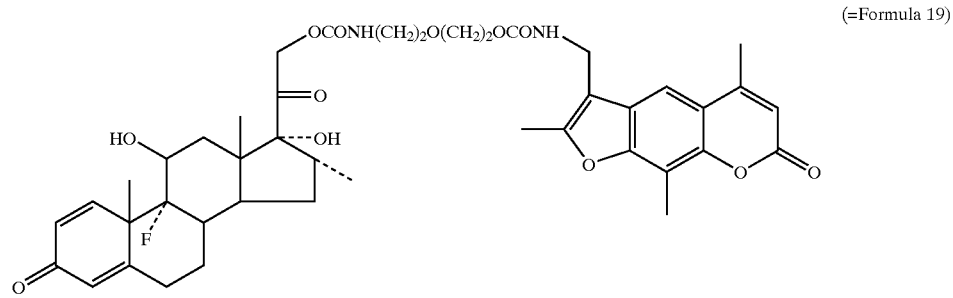
(=Formula 19)

8 mg compound of formula 20 are treated for 4 h in 2 ml DMF with 5 mg 4'-aminomethyltrioxalen hydrochloride and 15 µl NMM at 20° C. The mixture is then evaporated at 60° C. in a $N_2$-flow and the resulting residue chromatographed on silicagel. The product is eluated with AcOEt-MeOH (9:1)-mixture.

UV: 246 ($\epsilon$=33200), 295 ($\epsilon$=9600), 335 ($\epsilon$=6200).

Preparation of Starting Materials
Preparation of:

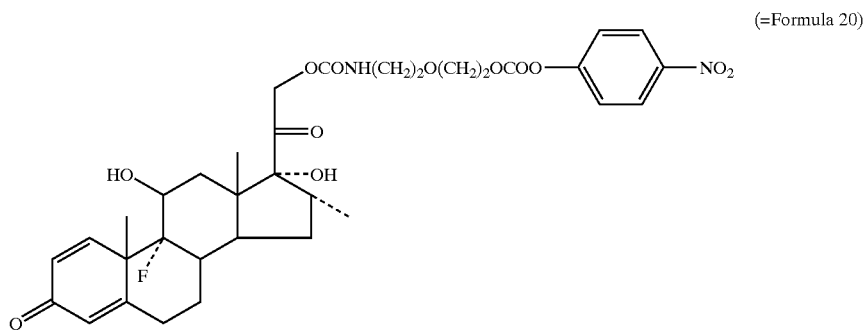

(=Formula 20)

250 mg compound of formula 21 are stirred for 4 h at room temperature in 7 ml THF with 208 µl NMM and 192 mg 4-nitrophenyl-chloroformic ester. After 4 h the solution is diluted with AcOEt, washed with 1 n aq. HCl-solution, sat. aq. NaCl-solution, dried over $Na_2SO_4$, evaporated and the crude material chromatographed on silicagel. The product is eluted with toluene-AcOEt(1:1)-mixture.

TLC: AcOEt, Rf=0.73, UV: 240 (ε=14100).

Preparation of:

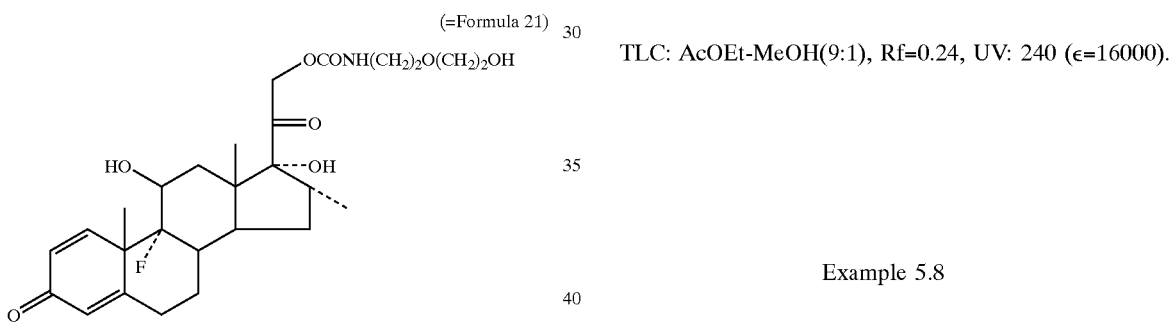

(=Formula 21)

430 mg dexamethasone-21-(4'-nitrophenyl-carbonate) (=Formula 11) are stirred for 3 h in 15 ml THF with 77.4 µl 2-(2-aminoethoxy)-ethanol at room temperature. The solution is diluted with AcOEt, washed with 1 n aq. HCl-solution, sat. aq. NaCl-solution, dried over $Na_2SO_4$, evaporated and the residue chromatographed on silicagel. The product is eluated with AcOEt.

TLC: AcOEt-MeOH(9:1), Rf=0.24, UV: 240 (ε=16000).

Example 5.8

Preparation of:

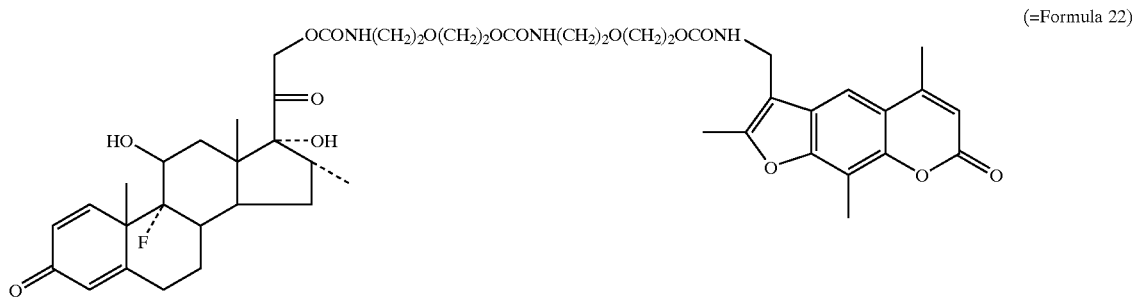

(=Formula 22)

A solution of 5 mg 4'-aminomethyltrioxalen hydrochloride in 2 ml DMF and 7.5 µl NMM is added to a solution of 14 mg compound of formula 23 dissolved in 1 ml THF. The mixture is stirred for 48 h at 20° C. and then evaporated at 60° C. in a $N_2$-flow. The resulting residue is chromatographed on silicagel. The product is eluated with EtOAc:MeOH (9:1).

TLC: EtOAc:MeOH (9:1), Rf=0.72, UV: 250 (ε=31900), 295 (ε=9750), 335 (ε6200).

Preparation Starting Materials
Preparation of:

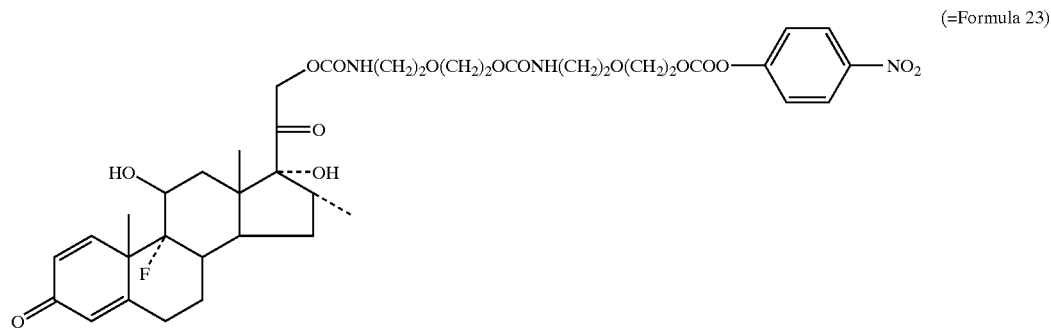
(=Formula 23)

80 mg compound of formula 24 are stirred for 4 h at room temperature in 4 ml THF with 26.8 µl NMM and 24.6 mg 4-nitrophenyl-chloroformic ester. After that the mixture is diluted with EtOAc, washed with 1 n HCl, sat. aq. NaHCO$_3$-solution, sat. aq. NaCl-solution and dried over Na$_2$SO$_4$. The crude material is purified by silicagel-chromatography. The product is eluated with EtOAc.

UV: 242 ($\epsilon$=14800).

Preparation of:

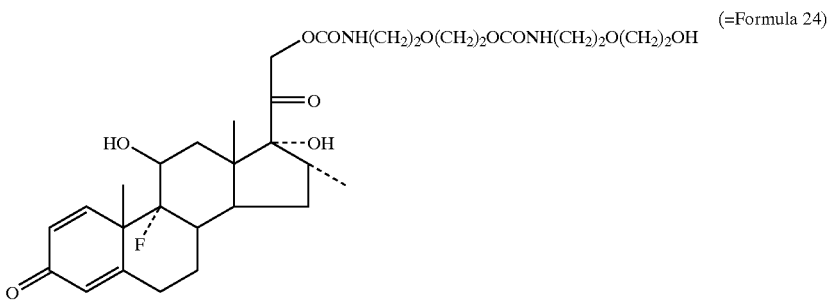
(=Formula 24)

100 mg compound of Formula 20 are stirred for 2 h at room temperature in 5 ml THF with 14.48 µl 2-(2-aminoethoxy)-ethanol. The solution is diluted with AcOEt, washed with 1 n HCl-solution, sat. aq. NaCl-solution, dried over Na$_2$SO$_4$, evaporated and the crude material chromatographed on silicagel. The product is eluted with AcOEt-MeOH(9:1)-mixture.

TLC: AcOEt-MeOH(9:1), Rf=0.51, UV: 242 ($\epsilon$=14000).

Example 5.9

Preparation of:

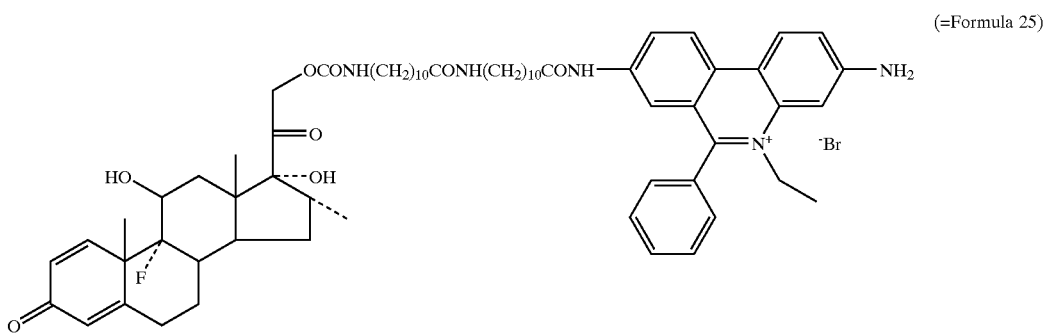
(=Formula 25)

and the other regioisomere relating to the aminogroups of the ethidiumbromide.

10 mg compound of Formula 16 dissolved in 1 ml THF are treated for 2 h at −20° C. with 3.3 µl isobuthylchloroformate in presence of 4.19 µl NMM. After 2 h a solution of 5 mg ethidiumbromide in 1 ml DMF and 4.19 µl NMM is added and stirred for 72 h at 20° C. The mixture is then evaporated at 6° C. in a N$_2$-flow, washed in 5 ml MeOH and again evaporated at 60° C. The product is purified by TLC (EtOAc:MeOH:Aceton=3:1:3 mixture; Rf=0.14); UV: 240 ($\epsilon$=14750), 298 ($\epsilon$=27100), 324 ($\epsilon$=11950).

Example 5.10

Preparation of:

(=Formula 26)

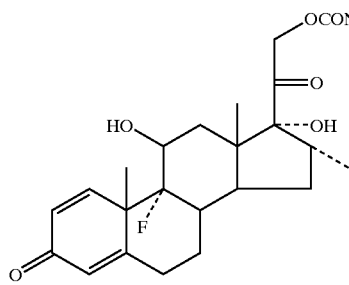
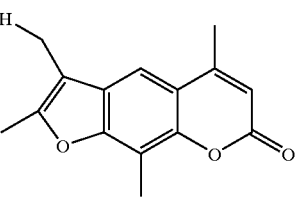

24 mg compound of formula 27 are treated for 2 h with 10 mg 4'-aminomethyltrioxalen hydrochloride and 9,4 µl NMM at 20° C. in 2 ml THF. The mixture is then evaporated at 60° C. in a N$_2$-flow and the resulting residue chromatographed on silicagel. The product is eluted with toluene-AcOEt(1:1)-mixture.

TLC: AcOEt, Rf=0,568, UV: 249 ($\epsilon$=33800), 296 ($\epsilon$=9600), 335 ($\epsilon$=6100).

Preparation of Starting Materials
Preparation of:

(=Formula 27)

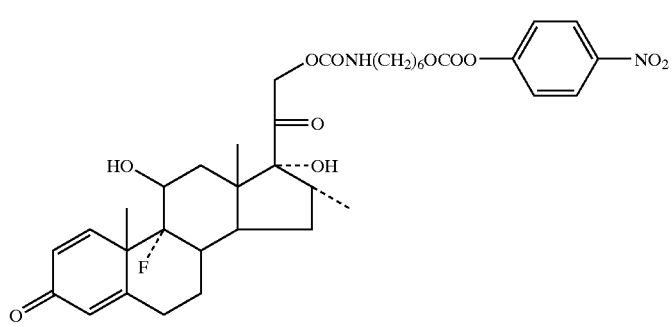

580 nm compound of formula 28 are stirred for 6 h at room temperature in 15 ml THF with 298 µl NMM and 428 mg 4-nitrophenyl-chloroformic ester. After 4 h the solution is diluted with AcOEt, washed with 1 n aq. HCl-solution, sat. aq. NaCl-solution, dried over Na$_2$SO$_4$, evaporated and the crude material chromatographed on silicagel. The product is eluted with AcOEt.

UV: 241 ($\epsilon$=13900).
Preparation of:

(=Formula 28)

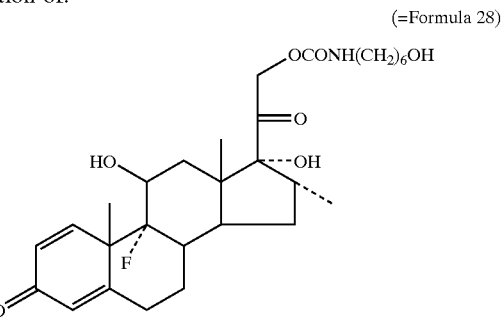

504 mg compound of formula 11 are stirred for 1 h in 30 ml THF with 118,5 mg 6-aminohexanol at room temperature. The solution is diluted with AcOEt, washed with 1 n aq. HCl-solution, sat. aq. NaCl-solution, dried over $Na_2SO_4$, evaporated and the residue chromatographed on silicagel. The product is eluted with AcOEt.

UV: 240 ($\epsilon$=15800).

Example 5.11

Preparation of:

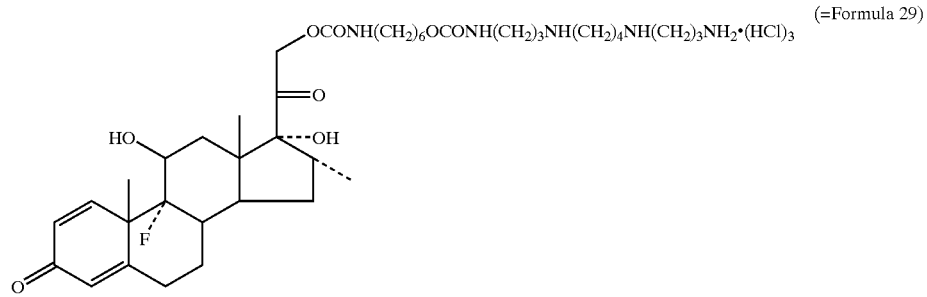
(=Formula 29)

88,4 mg compound of formula 27 in 1 ml DMF are added to a solution of 24,7 mg spermine in 1 ml DMF and stirred for 30 minutes. The mixture is then evaporated at 60° C. in a $N_2$-flow. The resulting residue is dissolved in water and acidified to pH 4.0 with 1 n HCl. The water solution is extracted with AcOEt and the water phase is liophilised.

UV: 240 ($\epsilon$=15000).

Example 5.12

Preparation of:

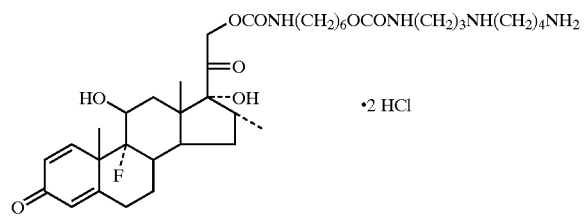
(=Formula 30)

180 mg compound of formula 27 in 1 ml DMF are added to a solution of 37.3 mg spermidine in 1 ml DMF and stirred for 30 minutes. The mixture is then evaporated at 60° C. in a $N_2$-flow. The resulting residue is dissolved in water and acidified to pH 4.0 with 1 n HCl. The water solution is extracted with AcOEt and the water phase is liophilised.

UV: 240 ($\epsilon$=6000).

Example 5.13

Preparation of:

(=Formula 31)

32,8 mg compound of formula 27 in 2 ml DMF are added to a solution of 19,8 mg linear polyethylenimin (Aldrich 46,853-3) in 1 ml DMF and stirred for 30 minutes. The mixture is then evaporated at 60° C. in a $N_2$-flow. The resulting residue is dissolved in water and acidified to pH 4.0 with 1 n HCl. The water solution is extracted with AcOEt and the water phase is liophilised.

UV: 240 ($\epsilon$=14300).

Example 5.14

Preparation of:

(=Formula 32)

42 mg compound of formula 27 in 1 ml DMF are added to a solution of 100 mg polyethylenimin (Aldrich 40,872-7) in 2 ml DMF and stirred for 30 minutes. The mixture is then evaporated at 60° C. in a N$_2$-flow. The resulting residue is dissolved in water and acidified to pH 4.0 with 1 n HCl. The water solution is extracted with AcOEt and the water phase is liophilised.

UV: 240 ($\epsilon$=2500).

Example 5.15

Preparation of:

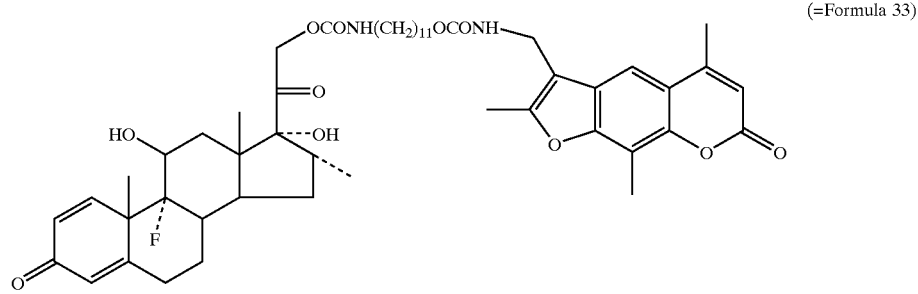

(=Formula 33)

A solution of 10 mg 4'-aminomethyltrioxalen hydrochloride in 1 ml DMF and 7,4 µl diisopropyl-ethylamin is added to a solution of 26,2 mg compound of formula 34 dissolved in 1 ml DMF. The mixture is stirred for 2 h at 20° C. and then evaporated at 60° C. in a N$_2$-flow. The resulting residue is chromatographed on silicagel. The product is eluated with toluene:EtOAc (1:1).

UV: 250 ($\epsilon$=31500), 295 ($\epsilon$=9400), 335 ($\epsilon$=6100).

Preparation of Starting Materials

Preparation of:

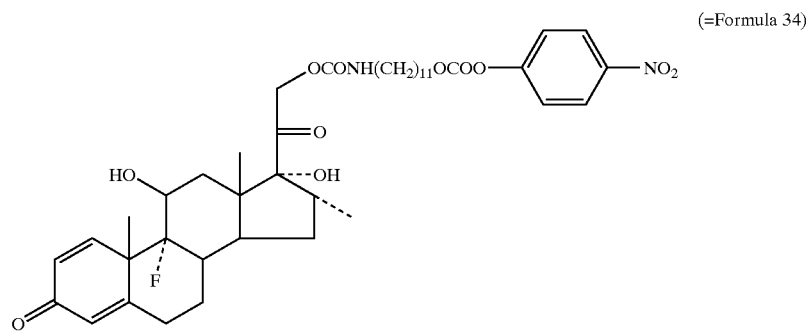

(=Formula 34)

330 mg compound of formula 35 are stirred for 2 h at room temperature in 10 dichlormethan with 171 µl diisoprpyl-ethylamin and 165 mg 4-nitrophenyl-chloroformic ester. After that the mixture is diluted with EtOAc, washed with 1 n HCl, sat. aq. NaHCO$_3$-solution, sat. aq. NaCl-solution, dried over Na$_2$SO$_4$ and evaporated. The crude material is purified by silicagel-chromatography. The product is eluated with toluene:EtOAc (4:1)-mixture.

UV: 242 ($\epsilon$=14500).

Preparation of:

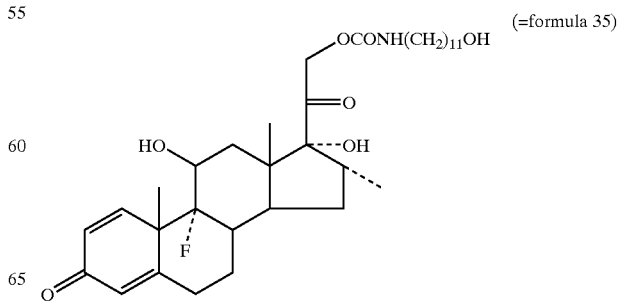

(=formula 35)

1 g compound of formula 11 is stirred for 18 h at room temperature in 8 ml THF and DMF (1:1)-mixture with 510 mg 11-amino-undecan-1-ol. The solution is diluted with AcOEt, washed with 1 n HCl-solution, water (10×), sat. aq. NaCl-solution, dried over $Na_2SO_4$ and evaporated. The crude material is chromatographed on silicagel. The product is eluated with toluene:EtOAc (2:1)-mixture.

UV: 241 ($\epsilon$=13900).

Example 5.16

Preparation of:

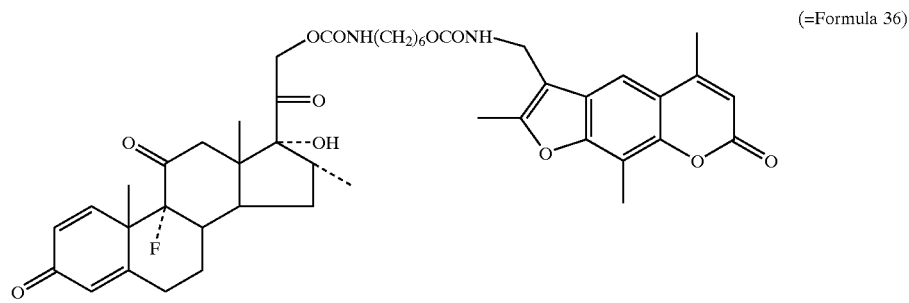

(=Formula 36)

12 mg of formula 36 are terated for 4 h with 5 mg 4'-aminomethyltrioxalen hydrochloride and 5,8 µl ethyldi-isopropylamine at 20 ° C. in 3 ml DMF. The mixture is then evaporated at 60° C. in a $N_2$-flow and the resulting residue chromatographed on silicagel. The product is eluated with loluene-AcOEt(1:1)-mixture.

TLC: AcOEt, Rf=0.62, UV: 250 ($\epsilon$=33500), 295 (t=950), 335 ($\epsilon$=6200).

Preparation of Starting Materials
Preparation of:

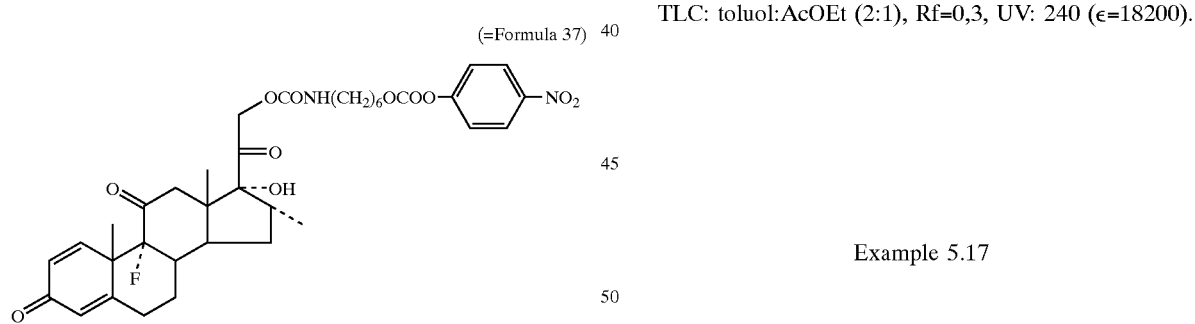

(=Formula 37)

70 m8 compound of formula 27 are treated with an excess of 8 n $CrO_3$ in 8 n aqueous $H_2SO_4$ in 20 ml aceton for 15 min. at 20° C. The excess of $CrO_3$ is destroyed by stirring with 1 ml methanol for 5 min. The reaction mixture is extracted with AcOEt, washed with saturated NaCl-solution, dried over $Na_2SO_4$, evaporated and the crude material chromatographed on silicagel. The product is eluted with toluol-AcOEt (1:1)-mixture.

TLC: toluol:AcOEt (2:1), Rf=0,3, UV: 240 ($\epsilon$=18200).

Example 5.17

Preparation of:

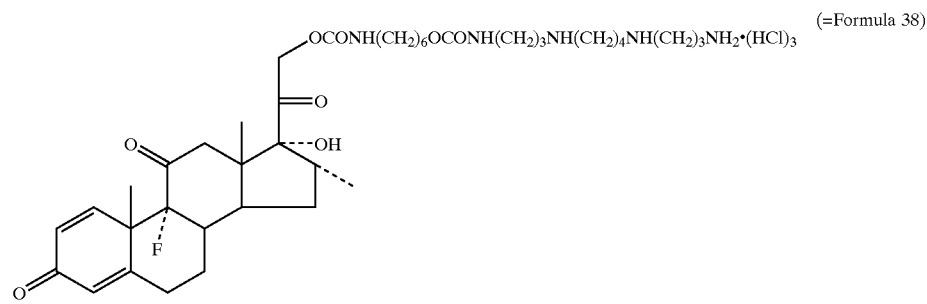

(=Formula 38)

17,3 mg compound of formula 37 in 1 ml DMF are added to a solution of 5 mg spermine in 1 ml DMF and stirred for 30 min. The mixture is then evaporated at 60° C. in a N$_2$-flow. The resulting residue is dissolved in water and acidified to pH 4.0 with 1 n HCl. The water solution is extracted with AcOEt and the water phase is liophilised.

UV: 241 ($\epsilon$=14800).

Example 5.18

Preparation

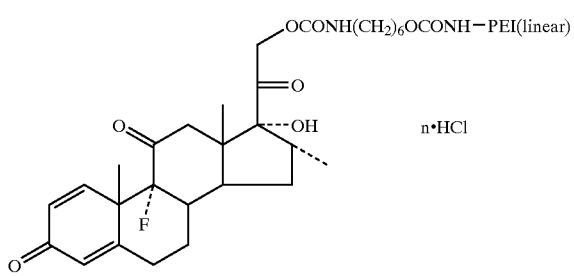
(=Formula 39)

6 mg compound of formula 37 in 2 ml DMF are added to a solution of 14 mg linear polyethylenimin (Aldrich 40,872-7) in 2 ml DMF and stirred for 30 min. The mixture is then evaporated at 60° C. in a N$_2$-flow. The resulting residue is dissolved in water and acidified to pH 4.0 with 1 n HCl. The water solution is extracted with AcOEt and the water phase is liophilised.

UV: 242 ($\epsilon$=2400).

Preparation of:

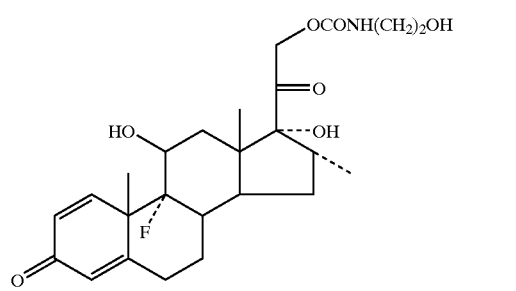
(=Formula 40)

220 mg compound of formula 11 aristirred for 45 minutes in 20 ml THF with 0,045 ml ethanolamine at room temperaturer. The solution is diluted with AcOEt, washed with 1 n aq. HCl-solution, sat. aq. NaCl-solution, dried over Na$_2$SO$_4$, evaporated and the residue chromatocraphed on silicagel. The product is eluted with AcOEt-MeOH(9:1).

TLC: AcOEt, Rf=0.70. UV: 239 ($\epsilon$=14500).

Example 5.19

Preparation of:

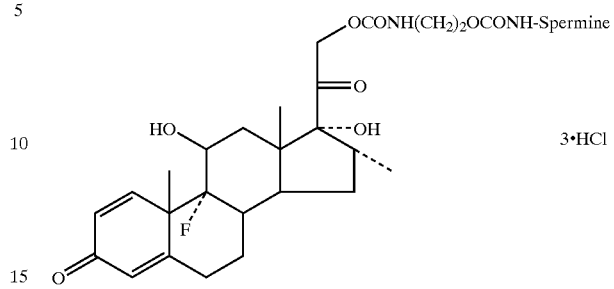
(=Formula 42)

18 mg compound of formula 41 in 1 ml DMF are added to a solution of 5,65 mg spermine in 68,4 µl DMF and stirred for 15 minutes. The mixture is then evaporated at 60° C. in a N$_2$-flow. The resulting residue is dissolved in water and acidified to pH 4.0 with 1 n HCl. The water-solution is extracted with AcOEt and the water phase is liophilised.

UV: 240 ($\epsilon$=17000).

Preparation of Starting Materials

Preparation of:

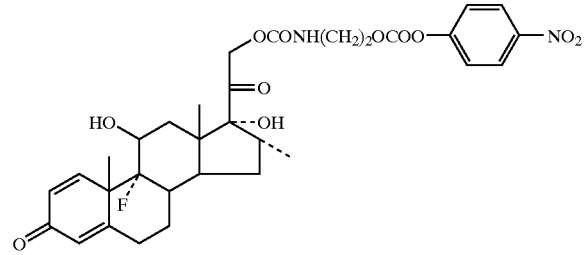
(=Formula 41)

180 mg compound of formula 40 are stirred for 26 hours at room temperature in 3 ml THF with 82,5 µl NMM and 104 mg 4-nitrophenyl-chloroformic ester. The solution is diluted with AcOEt, washed with 1 n aq. HCl-solution, sat. aq. NaCl-solution, dried over Na$_2$SO$_4$, evaporated and the crude material chromatographed on silicagel. The product is eluted with toluene-AcOEt(95:5)-mixture.

TLC: Toluene-AcOEt(3:1), Rf=0.56, UV: 241 ($\epsilon$=14900).

Example 5.20

Preparation of:

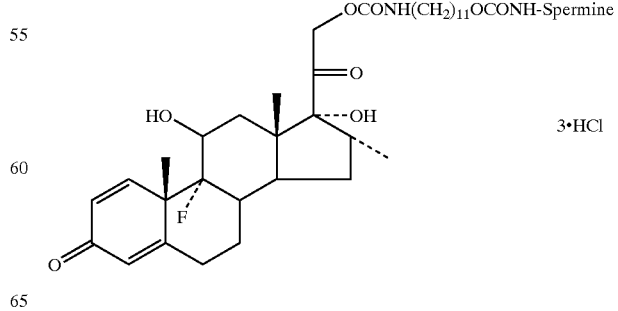
(=Formula 43)

59 mg compound of formula 34 in 2 ml DMF are added to a solution of 15,7 mg spermine in 1 ml DMF and stirred for 30 minutes. The mixture is then evaporated at 60° C. in a N$_2$-flow. The resulting residue is dissolved in water and acidified to pH 4.0 with 1 n HCl. The water solution is extracted with AcOEt and the water phase is liophilised.

UV: 241 ($\epsilon$=14900)

Example 6

Stability of C-21 Ester Versus C-21 Urethane Derivatives

Experimental Procedure:

The corticosteroids-derivatives (DEX-C$_4$-PSO and CL-HS-PSO) are incubated for 15 hours at 37° C. in a final concentration of 0.1 mM in 200 µl EtOH with:

a) cell extracts;

b) water buffered to pH 9;

c) water buffered to pH 5;

d) DMEW/10% FCS;

e) proteinase K (pH 7.8; 50 µg/ml);

f) dispase (2.4 U/ml).

After 15 hours of incubation each sample is separately extracted with 400 µl Ethyl acetate, evaporated under N$_2$-flow, redissolved in 20 µl Ethyl acetate and analysed by TLC analysis: stationary phase: Alugram SIL G-25 UV$_{254}$ (Macherey Nagel AG); mobile phase: Ethyl acetate-MeOH-Acetone (3-1-3).

The different spots are detected semiquantitatively by UV (254 nm) and compared with the following controls: Cortisol, CL-HS, CL-HS-PSO, DEX-C$_3$-COOH, DEX-O-OH, DEX-O-O-OH, DEX-O-O-PSO, Dexamethasone, CL-C$_{12}$-PSO and DEX-C$_4$-PSO respectively.

The urethane bond between the steroid moiety, the spacer and the DNA binder of DEX-C$_4$-PSO, CL-C$_{12}$-PSO and DEX-O-O-PSO is stable under acidic (pH 5) and alkaline (pH 9) conditions, by proteinase K (pH 7.8, 50 µg/ml) and dispase (2.4 U/ml) digestion and after incubation with cellular extracts and with DMEM/10% FCS.

However, the ester bond at position 21 of CL-HS-PSO is cleaved under the same conditions (5–10% cleavage), only by digestion with proteinase K and under acidic conditions is the ester bond stable.

The results of the stability tests are summarized in the following table:

| | water pH 5.0 | water pH 9.0 | dispase 2.4 U/ml in 1xPBS | proteinase K 50 µg/ml, pH 7.8 | cell extracts | DMEM/ 10% FCS |
|---|---|---|---|---|---|---|
| CL-C$_{12}$-PSO[b] | | | | | | |
| DEX-O-O-PSO[b] | | | | | | |
| DEX-C$_4$-PSO[b] | | | | | | |
| CL-HS-PSO[c] | ++[a] | ++[a] | | | +[a] | ++[a] |
| 100% EtOH | | | | | | |

[a]The degree of cleavage is estimated by TLC analysis (UV-detection at 254 nm);
[b]C-21 - urethane derivatives;
[c]C-21 - ester derivative Abbreviations:
CL=cortisol
DEX=dexamethasone
CL-HS=cortisol hemisuccinate
PSO=psoralen

DEX-C$_4$-PSO =

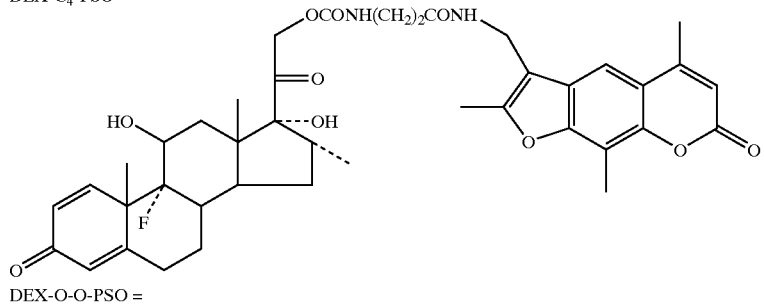

DEX-O-O-PSO =

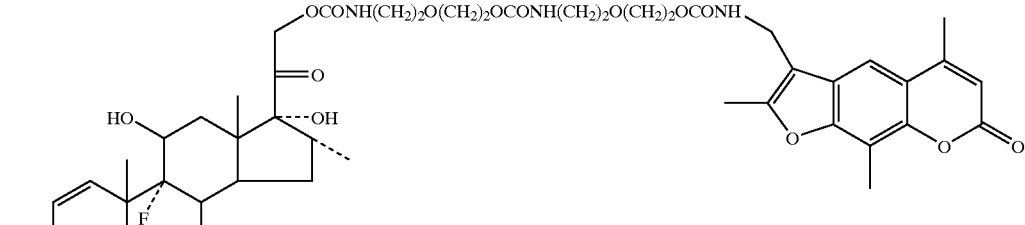

CL-C$_{12}$-PSO =

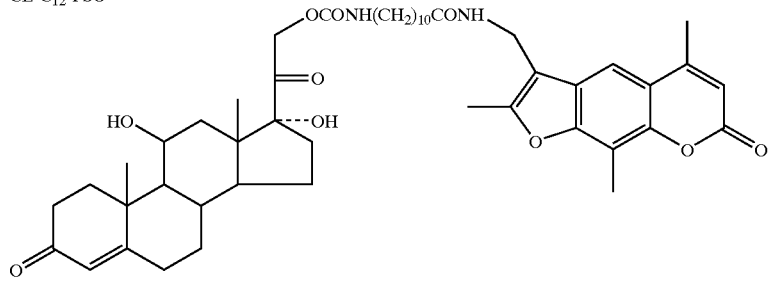

CL-HS-PSO = 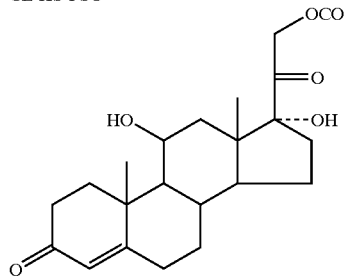

CL-HS = 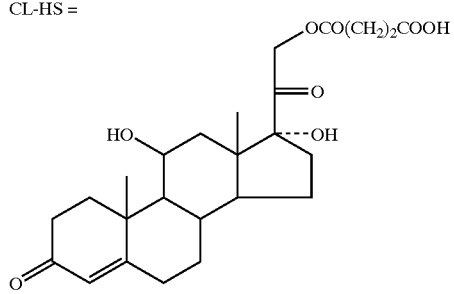

DEX-C$_3$-COOH = 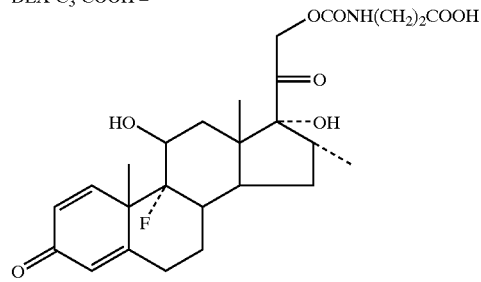

DEX-O-OH = 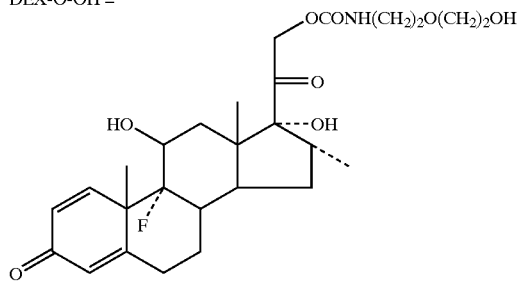

DEX-O-O-OH = 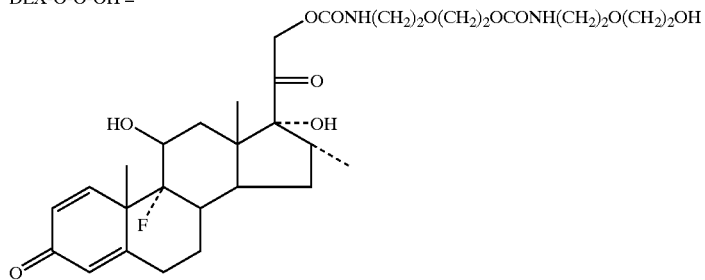

Example 7

In Vitro Competition Assay for Binding of Steroid Conjugates to Glucocorticoid Receptors (GR) of 3Y1 Cells 3Y1 were cultured in DMEM medium supplemented with 10% FCS at 37° C. and 5% $CO_2$. For the binding assay, cells were harvested and lysed in a hypotonic buffer (10 mM Tris pH 7.5, 10 mM NaCl, 1 mM EDTA, 10% glycerol, 10 mM sodium molybdate, 20 mM β-mercaptoethanol) in a dounce homogenizer (B-pestel). The cell extract was centrifuged at 10,000 9 for one hour. One hundred microliters (corresponding to the extract of 4×10$^6$ cells) were used for each sample. The samples were incubated in the same buffer but supplemented with 100 mM NaCl in presence of 4.5× 10$^{-9}$ M $^3$H-dexamethasone (81 Ci/mmol) and increasing amounts of unlabeled steroid competitors on ice for 2 hours. The reaction was stopped by adding active charcoal to a final concentration of 20 mg/ml in order to absorb excess, unbound steroids. The supernatant was spotted onto glass microfiber filters (Whatman 1822-025) and washed extensively in 20 mM Tris pH8, 1 mM EDTA, 40 mM NaCl. The filters were patted dry, introduced in counting vials with scintillation fluid and counted in a Tri- Carb 2000 CA beta-counter. Binding data are expressed as the percentage of specifc binding (n=3). 100% of specific binding corresponds to the amount of 4.5×10$^{-9}$ M $^3$H-dexamethasone in the absence of competitor.

The result of the IC50 (concentration of competitor needed to obtain 50% of competition of 3H-dexamethasone for the GR) values are given in the following tables:

a) Monourethane

| Conditions | | IC50 (conc.) |
|---|---|---|
| Ligand | Nr | |
| DEX-C23-Pso | 12 | $3.2.10^{-7}$M |
| DEX-C11-Pso* | 11 | $1.10^{-6}$M |
| DEX-C4-Pso | 10 | $4.10^{-7}$M |
| DEX-C23-EtBr | 09 | $5.10^{-8}$M |
| CL-C4-EtBr | 08 | $4.10^{-6}$M |
| DEX | 02 | $8.5.10^{-9}$M |
| CN | 01 | $8.10^{-7}$M | b) Diurethane

| Conditions | | IC50 (conc.) |
|---|---|---|
| Ligand | Nr | |
| DEX-C11-Sn | 07 | $9.10^{-7}$M |
| DEX-C6-Sn | 05 | $4.10^{-8}$M |
| DEX-C4-Sn | 05 | $8.5.10^{-7}$M |
| DEX-C11-Pso | 04 | $4.5.10^{-5}$M |
| DEX-C6-Pso | 03 | $2.5.10^{-7}$M |
| DEX | 02 | $8.5.10^{-9}$M |
| CN | 01 | $8.10^{-7}$M |

Abbreviations
EtBr Ethidium Bromide
Sn Spermine
DEX Dexamethasone
Pso 4'-Aminomethyltrioxsalen
CN Cortisone
DEX-C11-Sn compound of formula 43
DEX-C6-Sn compound of formula 30
DEX-C4-Sn compound of formula 42
DEX-C6-Pso compound of formula 26
DEX-C11-Pso compound of formula 33 (Diurethane)
DEX-C11-Pso compound of formula 12 (Monourethane)
DEX-C23-Pso compound of formula 15
DEX-C4-Pso compound of formula 8
DEX-C23-EtBr compound of formula 25
CL-C4-EtBr compound of formula 1

Example 8

8.1. Subcellular Localisation of GR-GFP Chimeras in the Presence of Various Monourethane Ligands: Nuclear Transfer Induction Assay (NTI)

Conditions: HeLa cells are transiently transfected by CaPO4 with an expression vector encoding a GR-GFP chimera (5 μg in transfection cocktail, 4 cm diameter dishes, DMEM with 3% FCS). After 24 hour expression, ligand is added for 1 hr and cells are fixed with formaldehyde (5 min 4° C.) and inspected by fluorescence microscopy. Fluorescent cells are counted and divided into different classes according to 'cytoplasmic' (C) versus 'nuclear' (N) localisation of fluorescence.

First column: "Conditions": Name of compounds added (marked at top: '//ligand'), and their concentration (in parentheses) and assay number (01 through 21). 2nd to 6th column: class subdivision; C>>N, C>N, C=N, C<N, C<<N.

Values are given as percentage of cells displaying the corresponding localisatidn, within each tested condition the sum is 100%.

Assay Number:

01, no ligand added: majority of cells show cytoplasmic fluorescence

02, Dexamethasone ($5\times10^{-7}$ M), strong nuclear fluorescence.

03, Dexamethasone ($5\times10^{-6}$ M), increased nuclear localisation

04–21, various compounds in which the steroid is derivatized (compound type is indicated at left) and tested at two concentrations ($10^{-7}$ M and $10^{-6}$ M)

Abbreviations:

CL Cortisol

DEX dexamethasone

CL-C3-COOH Cortisol-C4branch-with tree carboxyl-end; (compound of formula 2)

CL-C3-COOCH3 carboxymethylester derivate; (compound of formula 3)

CL-C4-EtBr Cortisol-C4-EtBr; (compound of formula 1)

CL-C4-Pso Cortisol-C4-Psoralen; (compound of formula 4)

DEX-C3-COOCH3 dexamethasone-C3-COOCH3 precursor; (compound of formula 10)

DEX-C4-Pso dexamethasone-C4-Psoralen; (compound of formula 8)

CL-C11-COOCH3 compound of formula 7

CL-C12-Pso compound of formula 5

DEX-C11-COOCH3 compound of formula 14

GR glucocorticoid receptor

GFP green fluorescent protein

EtBr ethidium bromide

All spacers are urethane based.

The results are summarized in the following table:

| Conditions | | | C>>N % | C>N % | C=N % | C<N % | C<<N % |
|---|---|---|---|---|---|---|---|
| Ligand | (conc.) | Nr | | | | | |
| DEX-C11-COOCH3 | ($1.10^{-6}$M) | 21 | 0 | 0 | 5 | 50 | 45 |
| DEX-C11-COOCH3 | ($1.10^{-7}$M) | 20 | 0 | 3 | 29 | 61 | 7 |
| CL-C12-Pso | ($1.10^{-6}$M) | 19 | 0 | 0 | 25 | 53 | 22 |

-continued

| Conditions | | C >> N % | C > N % | C = N % | C < N % | C << N % |
|---|---|---|---|---|---|---|
| CL-C12-Pso | (1.10-7M) | 18 | 5 | 40 | 52 | 3 | 0 |
| CL-C11-COOCH3 | (1.10-6M) | 17 | 0 | 3 | 24 | 60 | 13 |
| CL-C11-COOCH3 | (1.10-7M) | 16 | 5 | 20 | 55 | 20 | 0 |
| DEX-C4-Pso | (1.10-6M) | 15 | 0 | 20 | 60 | 15 | 5 |
| DEX-C4-Pso | (1.10-7M) | 14 | 20 | 35 | 40 | 5 | 0 |
| DEX-C3-COOCH3 | (1.10-8M) | 13 | 0 | 0 | 0 | 22 | 78 |
| DEX-C3-COOCH3 | (1.10-7M) | 12 | 0 | 0 | 0 | 25 | 75 |
| CL-C4-Pso | (1.10-6M) | 11 | 0 | 0 | 29 | 63 | 8 |
| CL-C4-Pso | (1.10-7M) | 10 | 0 | 20 | 75 | 5 | 0 |
| CL-C4-EtBr | (1.10-6M) | 09 | 0 | 0 | 55 | 45 | 0 |
| CL-C4-EtBr | (1.10-7M) | 08 | 0 | 17 | 74 | 9 | 0 |
| CL-C3-COOCH3 | (1.10-6M) | 07 | 0 | 1 | 2 | 55 | 42 |
| CL-C3-COOCH3 | (1.10-7M) | 06 | 0 | 1 | 21 | 50 | 18 |
| CL-C3-COOH | (1.10-6M) | 05 | 0 | 2 | 85 | 13 | 0 |
| CL-C3-COOH | (1.10-7M) | 04 | 0 | 55 | 43 | 2 | 0 |
| DEX | (1.10-6M) | 03 | 0 | 0 | 0 | 29 | 71 |
| DEX | (1.10-7M) | 02 | 0 | 0 | 3 | 30 | 67 |
| NO | (none) | 01 | 75 | 25 | 2 | 0 | 0 |

8.2. Subcellular Localisation of GR-GFP Chimeras in the Presence of Various Diurethane Ligands: Nuclear Transfer Induction Assay (NTI)

Conditions: CV-1 cells are transiently transfected with DOTAP (Boehringer-Mannheim) with an expression vector encoding a GR-GFP chimera (see 8.1). After 36 hours expression, ligand is added for 4 hr and cells are fixed and counted as given in 8.1.

| Conditions | | | C >> N % | C > N % | C = N % | C < N % | C << N % |
|---|---|---|---|---|---|---|---|
| Ligand | (conc.) | Nr | | | | | |
| DEX-C13-Sn | (5.10-6M) | 25 | 0 | 0 | 7 | 45.8 | 47.1 |
| DEX-C13-Sn | (5.10-7M) | 24 | 5.6 | 32.4 | 56 | 6 | 0 |
| DEX-C13-Sn | (5.10-8M) | 23 | 16.7 | 61.4 | 21.9 | 0 | 0 |
| DEX-C13-Sn | (5.10-9M) | 22 | 19.5 | 64.5 | 15.9 | 0 | 0 |
| DEX-C8-Sn | (5.10-6M) | 21 | 0 | 0 | 0.5 | 7.5 | 92 |
| DEX-CB-Sn | (5.10-7M) | 20 | 0 | 1.4 | 6.6 | 25.1 | 66.8 |
| DEX-C8-Sn | (5.10-8M) | 19 | 0 | 3.6 | 27.6 | 29.1 | 39.8 |
| DEX-C8-Sn | (S.10-9M) | 18 | 17.1 | 39.2 | 30.8 | 11.8 | 1.1 |
| DEX-C4-Sn | (5.10-6M) | 17 | 0 | 0 | 2.9 | 27.6 | 69.5 |
| DEX-C4-Sn | (5.10-7M) | 16 | 12 | 15.4 | 67.4 | 4.6 | 0.6 |
| DEX-C4-Sn | (5.10-8M) | 15 | 19.8 | 35.8 | 43.3 | 1.1 | 0 |
| DEX-C4-Sn | (5.10-9M) | 14 | 27.7 | 43.8 | 28.5 | 0 | 0 |
| DEX-C13-Ps | (5.10-6M) | 13 | 0 | 0 | 1.9 | 53.1 | 45 |
| DEX-C13-Pso | (5.10-7M) | 12 | 1.3 | 25.7 | 58.3 | 14.8 | 0 |
| DEX-C13-Pso | (5.10-8M) | 11 | 8.1 | 37.1 | 52.9 | 1.9 | 0 |
| DEX-C13-Pso | (5.10-9M) | 10 | 9.4 | 52.9 | 34.2 | 3.6 | 0 |
| DEX-C8-Pso | (5.10-6M) | 09 | 0 | 0 | 0 | 10 | 90 |
| DEX-C8-Pso | (5.10-7M) | 08 | 0 | 0 | 0 | 6 | 94 |
| DEX-C8-Pso | (5.10-8M) | 07 | 0 | 0 | 9.8 | 29.4 | 60.8 |
| DEX-C8-Pso | (5.10-9M) | 06 | 0 | 3.5 | 35.7 | 38.3 | 22.6 |
| DEX | (5.10-6M) | 05 | 0 | 0 | 0 | 0.5 | 99.5 |
| DEX | (5.10-7M) | 04 | 0 | 0 | 0 | 1 | 99 |
| DEX | (5.10-8M) | 03 | 0 | 0 | 0 | 5 | 95 |
| DEX | (5.10-9M) | 02 | 0 | 0 | 0.3 | 42.1 | 57.5 |
| no | (none) | 01 | 41 | 56 | 4 | 0 | 0 |

Assay Number:

01, no ligand added: majority of cells show cytoplasmic fluorescence

02–05, Dexamethasone at four different concentrations ($5 \times 10^{-6}$ M, $5 \times 10^{-7}$ M, $5 \times 10^{-8}$ M and $5 \times 10^{-9}$ M)

06–25, various compounds in which the steroid is derivatized (compound type is indicated at left) and tested at four concentrations ($5 \times 10^{-6}$ M, $5 \times 10^{-7}$ M, $5 \times 10^{-8}$ M and $5 \times 10^{-9}$ M)

Abbreviations

Sn Spermine
Sd Spermidine
DEX Dexamethasone
Pso 4'-Aminomethyltrioxsalen
DEX-C8-Sn compound of formula 29
DEX-C13-Sn compound of formula 43
DEX-C4-Sn compound of formula 42
DEX-CS-Pso compound of formula 26
DEX-C13-Pso compound of formula 33

Example 9

Transfection Enhancement by CLC4EtBr

Conditions: 3Y1 cells are transfected with an expression vector that is constitutively expressing the reporter gene LacZ (CMV-LacZ). Transfection conditions are identical throughout the various samples (total 10–12 μq DNA for 4 cm dishes). In some samples the DNA used for the transfection cocktail is pre-incubated with various conjugates at the given concentrations. The concentrations are calculated to give from 10-8 to 10-6 M after dispersing the CaPO4 precipitate in the recipient dish (5 ml volume). Transfection is performed O/N and after rinsing of the precipitate the cells are further incubated for 24 hours. LacZ levels are determined from cell extracts with a chemiluminescence LacZ enzyme assay (Galactolight plus. Tropix). The relative luminescence from each extract is given in RLU/mg*1000.

Transfection Conditions for DNA/corlisol-C4-ethidium Mix:

Materials:
   DNA: CsCI purified CMVIacZ plasmid (10 kb) resuspended in TE (10 mM Tris.HCl, pH 7.6, 1 mM EDTA) at a concentration of 500 nanogram/microliter
   Hormone-derivative stock: cortisol-C4-ethidium resuspended in 100% ethanol at a concentration of 10 exp(-3) M
   Ca ++ mix: 0.5 M $CaCl_2$, 50 mM HEPES.HCl, pH 7.05
   Pi-mix: 0.75 mM NaH2-P04, 0.75 mM Na2HPO4.50 mM HEPES.HCl pH 7.05

Procedure:
   Cell culture. Cells are cultivated in DMEM supplemented with serum and antibiotica according to standard conditions (typically 10% FCS and Pen/Strep as antibiotica). At the day of transfection, cells are trypsinized and seeded at around 25–30% confluency. Cells are allowed to adhere to dish for 4–6 hours prior to transfection.

DNA pre-incubation (example for conditions that give5× 10 exp (-6) Molar final concentration of the CL-C4-EtBr conjugate):
   5 microgram of CMV-LacZ DNA (in 10 microliter TE) are mixed with 10 nmoles of hormone derivative (10 microliters stock solution) and incubated for 10 min at room temperature (final volume: 20 ul). The DNA/cortisol-C4-ethidum mix is then supplemented with 7 micrograms sheared calf thymus carrier DNA (in 14 microliters TE) and bidistilled water to give a final volume of 125 microliters.

Transfection by CaPO4: to each transfection sample (125 microliter volume DNA+water). 125 microliters of Ca ++ mix are added, and the mix is incubated for 5–10 min at room temperature. Each sample is then supplemented with 250 microliter of Pi-mix (with simultaneous mixing by up-down pipetting) and is further incubated 10 minutes at room temperature after which the cocktail is poured on top of the medium (5 ml) of each cell culture dish (4 cm diameter). The optimal time of incubation after Pi-mix addition is pre-determined by prior evaluation (size of the precipitate) of parallel samples. The precipitate is allowed to deposit onto the cells for 15 hours (incubation of 37 degrees, 5% CO2). The cells are then rinsed twice with Tris-buffered Saline, supplemented with fresh medium and further incubated under standard conditions. To analyze LacZ reporter gene function, the cells are either fixed or harvested 24 hours after precipitate removal.

Variation of parameters: samples in which the C1–C4-EtBr conjugates (or control compounds) are used at different concentrations, are similarly treated, except that the concentration of the stock solution in ethanol is correspondingly varied.

Abbreviations:
   rep=reporter gene construct
   Cn=cortisone
   other symbols as in Example 7.

Lanes:
   01, no CMVLacZ plasmid transfected (endogenous basal)
   02, plasmid transfected, no pretreatment of DNA (basal level)
   03–16, plasmid transfected, different compounds added in transfection cocktail
   03, free cortisone given in medium during transfection (negative control)
   04, Ethanol as negative control for solvent (0.01%)
   5–7, CL-21-urethane branched with free COOCH3
   8–10, CL-21-urethane-Etbr (4 atoms spacer) preincubated with DNA
   11–13, CL-21-urethane branched+equimolar EtBr (true negative control)
   14–16, EtBr alone (further negative control)

Note the strong improvement (5–7 fold) of expression in lane 10 versus lanes 11–13. With the cell line 3Y1 that contains substantial amounts of GR we obtained analogous results in several independent experiments, suggesting that the SMGD effect is seen when using the conjugates CL-urethane-EtBr.

The results are summarized in the following table:

| conditions | | | light units |
|---|---|---|---|
| rep. | //Ligand (conc.) | Nr | |
| 5 μg | //EtBr (10-6M) | 16 | 2250 |
| 5 μg | //EtBr (10-7M) | 15 | 2500 |
| 5 μg | //EtBr (10-8M) | 14 | 2750 |
| 5 μg | //CL-C4 & EtBr (10-6M) | 13 | 1250 |
| 5 μg | //CL-C4 & EtBr (10-7M) | 12 | 1000 |
| 5 μg | //CL-C4 & EtBr (10-8M) | 11 | 2000 |
| 5 μg | //CL-C4EtBr (10-6M) | 10 | 7250 |
| 5 μg | //CL-C4EtBr (10-7M) | 09 | 3750 |
| 5 μg | //CL-C4EtBr (10-8M) | 08 | 2750 |
| 5 μg | //CL-C4 (10-6M) | 07 | 3750 |
| 5 μg | //CL-C4 (10-7M) | 06 | 1625 |
| 5 μg | //CL-C4 (10-8M) | 05 | 2500 |
| 5 μg | //EtOH equiv | 04 | 3625 |
| 5 μg | //Cn (10-6M) | 03 | 5375 |
| 5 μg | //no | 02 | 2125 |
| 5 μg | //no (10-6M) | 01 | 250 |

Example 10

Transfection Enhancement by CLC4EtBr In CV-1 Cells Reconstituted with Exogenous GR Conditions: CV-1 cells are first infected with an adenovirus system allowing expression of GR in >90% of the cells (S. B. Verca, unpublished). After 24 hours the cells are; transfected with an expression vector that is constitutively expressing the reporter gene LacZ (CMV-LacZ). Transfection conditions and analysis of LacZ reporter are the same as described in Example 7 legend. Transfection is performed O/N and after rinsing of the precipitate the cells are further incubated for 24 hours. LacZ levels are determined from cell extracts with a chemiluminescence LacZ enzyme assay (Galactolight plus, Tropix). The relative luminescence from each extract is given. Each value represents an individual extract. "Induction": relative reporter gene activity (values divided by value of assay in lane 9, true negative control for liganding), rel/RLU=(RLU:protein)×1000, net=rel/RLU–600 (600=rel/RLU value approximately corresponding to rel/RLU value of mock transfection).

Symbols: as in Examples 7 and 8.
Lanes:
  01, 02 no reporter plasmid or mock plasmid transfected (endogenous basal)
  03 CMV-LacZ plasmid transfected, no pretreatment of DNA (basal level)
  04–14, plasmid transfected, different compounds added in transfection cocktail
  04–06, DNA preincubated with CL-21-urethane EtBr conjugate
  07–09, DNA incubated with CL-21-urethane plus equimolar EtBr (true negative control)
  10–11, EtBr alone (further negative control)

Note the very strong improvement (15–20 fold) of expression in lane 06 versus lanes 7–9. No SMGD effect is seen when we use CV-1 cells that have not been supplemented with GR (data not shown in this figure, but repeated in several experiments by the teams in Bern and in Fribourg). This means that the SMGD effect is dependent on the presence of the cognate receptor, thus giving the formal proof that SMGD is an intracellular receptor-mediated, specific mechanism.

The results are summarized in the following table:

| conditions | | | RLU | protein | rel/RLU | net | induction |
|---|---|---|---|---|---|---|---|
| rep. | //Ligand (conc.) | Nr | | | | | |
| ok | //EtBr (10-6) | 11 | 851 | 694 | 1226.2 | 626.2 | 0.77 |
| ok | //EtBr (10-7) | 10 | 1632 | 733 | 2226.5 | 1626 | 2.01 |
| ok | //CLC4 & EtBr (10-6) | 09 | 982 | 696 | 1410.9 | 810.9 | 1 |
| ok | //CLC4 & EtBr (10-7) | 08 | 1087 | 654 | 1662.1 | 1062 | 1.31 |
| ok | //CLC4 & EtBr (10-8) | 07 | 794 | 677 | 1172.8 | 572.8 | 0.71 |
| ok | //CLC4EtBr (10-6) | 06 | 10010 | 686 | 14592 | 13992 | 17.3 |
| ok | //CLC4EtBr (10-7) | 05 | 1988 | 702 | 2831.9 | 2232 | 2.75 |
| ok | //CLC4EtBr (10-8) | 04 | 1211 | 723 | 1675 | 1075 | 1.33 |
| ok | //none (none) | 03 | 1424 | 716 | 1988.8 | 1389 | 1.71 |
| mock | //none (none) | 02 | 410 | 679 | 603.83 | 3.829 | 0 |
| no | //no (none) | 01 | 413 | 661 | 624.81 | 24.81 | 0.03 |

Conditions: HUH-7 cells are human hepatoma cells that contain substantial amounts of glucocorticoid receptor. The cells are transfected with an expression vector that is constitutively expressing the reporter gene LacZ (CMV-LacZ). Transfection conditions and analysis of LacZ reporter are the same as described in Example 7 legend. Transfection is performed O/N and after rinsing of the precipitate the cells are further incubated for 24 hours. LacZ levels are determined from cell extracts with a chemiluminescence LacZ enzyme assay (Galactolight plus, Tropix). The relative luminescence from each extract is given. Each value represents an individual extract. "Induction": relative reporter gene activity (values divided by value of assay in lane 9, true negative control for DNA liganding). rel/RLU= (RLU:protein)×1000; net=rel/RLU−600 (600=rel/RLU value approximately corresponding to rel/RLU value of mock transfection).

Legend: as in Examples 7 and 8.

Lanes:

01,02 no reporter plasmid or mock plasmid transfected (endogenous basal)
  03 CMV-LacZ plasmid transfected, no pretreatment of DNA (basal level);
  04–12, plasmid transfected, different compounds added in transfection cocktail
  04–05, free dexamethasone in medium (verify unspecific boost of expression)
  06–07, DNA preincubated with CL-21-urethane-EtBr conjugate
  08–09, DNA incubated with CL-21-urethane plus equimolar EtBr (true negative control)
  10, EtBr alone (further negative control)

Note the clear improvement (7–8 fold) of expression in lane 07 versus lanes 8–9. This results indicates that the SMGD effect is seen in a different cell line than the original 3Y1, indicating that it is not necessarily cell-line specific.

The results are summarized in the following table:

| conditions | | | RLU | protein | rel/RLU | net | induction |
|---|---|---|---|---|---|---|---|
| rep. | //Ligand (conc.) | Nr | | | | | |
| ok | //EtBr (10-6) | 10 | 168920 | 724 | 233.314917 | 103 | 1.49 |
| ok | //CLC4 & EtBr 10-6) | 09 | 135911 | 682 | 199.282991 | 69.3 | 1 |
| ok | //CLC4 & EtBr 10-7) | 08 | 274779 | 884 | 310.835973 | 181 | 2.61 |
| ok | //CLC4EtBr (10-6) | 07 | 629514 | 935 | 673.277005 | 543 | 7.84 |
| ok | //CLC4EtBr (10-7) | 06 | 198082 | 747 | 265.170013 | 135 | 1.95 |
| ok | //Dex (10-6) | 05 | 238837 | 759 | 314.673254 | 185 | 2.67 |
| ok | //Dex (10-7) | 04 | 263704 | 738 | 357.322493 | 227 | 3.28 |
| ok | //none (none) | 03 | 229367 | 732 | 313.342896 | 183 | 2.65 |
| mock | //none (none) | 02 | 93955 | 679 | 138.372607 | 8.37 | 0.12 |
| no | //no (none) | 01 | 100100 | 661 | 151.437216 | 21.4 | 0.31 |

Example 12

DNA/cortisol-C4-psoralen Cross-linking Conditions
Materials:
  DNA: CsCl purified pBR322, linearized with HindIII and resuspended in TE at a concentration of 30 nanogram/microliter
  hormone derivative: cortisol-C4psoralen resuspended in 100% methanol at a concentration of 10 exp(−3) Molar
  psoralen (Fluka) resuspended in 100% ethanol at a concentration of 10 exp(−3)Molar.
  Irradiation buffer: 50 mM Tris (pH=7.5), 0.1 mM EDTA, 10 mM NaCl, 10 mM MgCl2
  crosslinker apparatus: Bio-Link (BLX) equipped with 4 UV lamps (T-8.L, 365 nanometer nominal wave length)
  96× wells (250 microliter/well) plate in polystyrene (TPP)
Procedure:

1 microgram of DNA (in 33 microliter) is mixed at room temperature with 5 nmoles cortisol-C4-psoralen or plain psoralen (either in 5 microliter) and 33 microliter irradiation buffer and pipetted into a well (final volume: 71 microliter) The 96× wells plate is then covered by its plastic lid and put on top of an ice-bed in a plastic box inside the crosslinker apparatus. The cooled microwell plate is irradiated for 20 min with 365 nm UV light (corresponds to an approximate value of 16 joules/square cm). The cross-linked products are then precipitated 2 times with ethanol and resuspended in TE. The products are compared to non-irradiated samples by alkaline gel electrophoresis, where cross-linked DNA maintains its double-stranded molecular weight. Cross-linking with cortisol-C4-psoralen is found to be as efficient as cross-linking with free psoralen.

List of References

Chu et al. (1987), Nucl. Acids Res. 15: 1311–1326;
Hodgson and Solaiman (1996), Nature Biotech. 14: 339–342
Shillito et al. (1985), Bio Technology 3: 1099–1103
Schocher R J et at, Bio/technology, 4: 1093–1096 (1986)
Wang Y-C et at, Plant Mol. Biol. 11: 433–439 (1988)
EP-A-434,616
Larrick and Burck, Gene Therapy: Application of Molecular Biology, Elsevier Science Publ. Co., Inc., New York, N.Y. (1991)
Kriegler, Gene Transfer and Expression: A Laboratory Manual, W. H. Freeman and Company, New York (1990)
International Application No. WO 95/11984
Kimura et al., Int J Cancer 15,694,706, 1975
Satoh et al., Nucl Acids Res 21, 4429–4430,1993
Boussif et al., PNAS USA 92, 7297–7301, 1995

What is claimed is:

1. A compound comprising a steroid hormone selected from the group consisting of glucocorticoid hormones, mineralcorticoid hormones, androgens and estrogens, said steroid hormone being stably linked via a spacer of 5–15 atoms to a psoralen, wherein the steroid hormone is linked via a first urethane bond to the spacer and the spacer, is linked via a second urethane bond to the psoralen.

2. The compound of claim 1, wherein the spacer contains 9—11 atoms.

3. The compound of claim 1, wherein the first urethane bond is positioned either at carbon atom 6 or 21 of the glucocorticoid hormone.

4. The compound of claim 1, wherein the spacer contains 10 atoms.

5. The compound of claim 1, wherein the steroid hormone is a glucocorticoid hormone.

6. The compound of claim 5, wherein the glucocorticoid hormone is selected from dexamethasone and cortisol.

7. The compound of claim 5, wherein the first urethane bond is positioned at any one of carbon atoms 1, 2, 4, 6, 7, 11α, 12, 15, 16, 17 or 21 of the glucocorticoid hormone.

8. A method for the preparation of the compound according to claim 1 comprising the steps of ligating a spacer of 5–15 atoms to the steroid hormone via an urethane bond and ligating the DNA incorporating molecule psoralen via an urethane bond to the spacer.

* * * * *

UNITED STATES PATENT AND TRADEMARK OFFICE
CERTIFICATE OF CORRECTION

PATENT NO.    : 6,753,424 B1
DATED         : June 22, 2004
INVENTOR(S)   : Frey et al.

It is certified that error appears in the above-identified patent and that said Letters Patent is hereby corrected as shown below:

Column 50,
Line 18, after "first urethane bond to the spacer and" please delete "the spacer, is linked" and insert -- the spacer is linked -- in its place.
Line 37, after "ligating the" please delete "DNA incorporating molecule."

Signed and Sealed this

Thirtieth Day of November, 2004

JON W. DUDAS
*Director of the United States Patent and Trademark Office*